US010264859B2

(12) United States Patent
Parker et al.

(10) Patent No.: US 10,264,859 B2
(45) Date of Patent: Apr. 23, 2019

(54) LIQUID DISPENSER DEVICE THAT CAN BE WORN AS JEWELRY

(71) Applicants: Ivonne Parker, Bakersfield, CA (US); Adonica Vickers, Bakersfield, CA (US)

(72) Inventors: Ivonne Parker, Bakersfield, CA (US); Adonica Vickers, Bakersfield, CA (US)

( * ) Notice: Subject to any disclaimer, the term of this patent is extended or adjusted under 35 U.S.C. 154(b) by 0 days.

(21) Appl. No.: 15/823,180

(22) Filed: Nov. 27, 2017

(65) Prior Publication Data

US 2018/0078011 A1    Mar. 22, 2018

Related U.S. Application Data

(63) Continuation-in-part of application No. 14/556,548, filed on Dec. 1, 2014.

(60) Provisional application No. 61/913,377, filed on Dec. 8, 2013.

(51) Int. Cl.
| | |
|---|---|
| *B05B 1/00* | (2006.01) |
| *A44C 15/00* | (2006.01) |
| *B05B 11/04* | (2006.01) |
| *A44C 9/00* | (2006.01) |
| *A44C 25/00* | (2006.01) |
| *A61L 2/18* | (2006.01) |
| *B05B 11/00* | (2006.01) |
| *B05B 15/62* | (2018.01) |
| *B05B 1/04* | (2006.01) |
| *A44C 5/00* | (2006.01) |

(52) U.S. Cl.
CPC .......... *A44C 15/002* (2013.01); *A44C 9/0069* (2013.01); *A44C 25/002* (2013.01); *A61L 2/18* (2013.01); *B05B 11/007* (2013.01); *B05B 11/0054* (2013.01); *B05B 11/048* (2013.01); *B05B 15/62* (2018.02); *A44C 5/003* (2013.01); *A44C 15/005* (2013.01); *B05B 1/044* (2013.01)

(58) Field of Classification Search
CPC ... B05B 15/62; B05B 11/0054; B05B 11/007; B05B 11/048; A44C 9/0069; A44C 25/002; A61L 2/18
USPC ........................................................ 222/175
See application file for complete search history.

(56) References Cited

U.S. PATENT DOCUMENTS

| | | | |
|---|---|---|---|
| 1,190,905 | A | 7/1916 | Jasper |
| 1,490,496 | A | 4/1924 | Trevillian |
| 1,584,205 | A | 5/1926 | Zaldo |

(Continued)

*Primary Examiner* — Patrick M Buechner
*Assistant Examiner* — Michael J Melaragno
(74) *Attorney, Agent, or Firm* — Matthew C. McCartney; Eastman McCartney Dallmann LLP

(57) ABSTRACT

The Liquid Dispenser that can be worn as jewelry of the present invention includes a dispenser having a bladder assembly and an outer shell. The outer shell opens to receive the bladder assembly, which includes a flexible bladder, neck and valve. The outer shell has an opening, exposing the enclosed flexible bladder to enable a user to apply pressure directly on the flexible bladder through the opening. When a user applies pressure to the flexible bladder, liquid passes through the valve for use. In an alternative embodiment, a flexible bladder is contained within a watch base. The watch base includes a flexible watch face that when pressed by a user, applies pressure to the flexible bladder. In yet another embodiment, a pump/valve device in combination with hollow tubes that store liquid enables a user to press a flexible dome on the device to release fluid stored in the hollow tubes.

6 Claims, 18 Drawing Sheets

(56) References Cited

U.S. PATENT DOCUMENTS

| | | | | |
|---|---|---|---|---|
| 1,632,890 | A | 6/1927 | Pamphilis | |
| 1,683,545 | A * | 9/1928 | Harris | A44C 15/002 2/300 |
| 1,861,644 | A | 6/1932 | Roberts | |
| 2,235,350 | A | 3/1941 | Anderson | |
| 2,432,288 | A | 12/1947 | Danziger | |
| 2,473,226 | A | 6/1949 | Sheldon | |
| 3,405,843 | A | 10/1968 | Watson, Jr. | |
| 3,876,112 | A * | 4/1975 | Kramer | B65D 1/04 220/23.4 |
| 4,023,712 | A | 5/1977 | Babiak | |
| 4,058,237 | A | 11/1977 | Luke | |
| 4,058,972 | A | 11/1977 | Weick | |
| 4,133,457 | A * | 1/1979 | Klassen | B65D 47/2031 137/849 |
| 4,168,032 | A | 9/1979 | Sneider | |
| D281,666 | S | 12/1985 | Fay, Sr. | |
| 4,736,876 | A | 4/1988 | Kriss | |
| 4,768,688 | A | 9/1988 | Harrigan | |
| 4,932,566 | A | 6/1990 | Weinbaum | |
| D315,245 | S | 3/1991 | Envall | |
| D323,430 | S | 1/1992 | Niederkorn | |
| 5,088,624 | A | 2/1992 | Hackett | |
| 5,217,143 | A | 6/1993 | Aitken | |
| 5,232,664 | A | 8/1993 | Krawzak | |
| 5,261,570 | A | 11/1993 | Hippely | |
| 5,307,955 | A | 5/1994 | Viegas | |
| 5,316,182 | A | 5/1994 | Lee | |
| 5,358,144 | A | 10/1994 | Mock | |
| 5,474,212 | A | 12/1995 | Ichikawa | |
| 5,516,005 | A | 5/1996 | Moseley | |
| 5,815,467 | A | 9/1998 | Deering | |
| D408,988 | S | 5/1999 | Barber | |
| 5,924,601 | A | 7/1999 | Chen | |
| 5,927,347 | A | 7/1999 | Villaveces | |
| 5,927,548 | A * | 7/1999 | Villaveces | A45F 5/02 222/175 |
| 5,940,349 | A | 8/1999 | Stewart | |
| 5,957,347 | A | 9/1999 | White | |
| 6,002,651 | A | 12/1999 | Baccaray | |
| 6,082,593 | A | 7/2000 | Borcherds | |
| 6,126,041 | A | 10/2000 | Di Tomasso | |
| 6,142,344 | A | 11/2000 | Kai | |
| 6,312,411 | B1 | 11/2001 | Kanai | |
| 6,340,242 | B1 | 1/2002 | Sandidge | |
| 6,405,897 | B1 | 6/2002 | Jepson | |
| 6,460,781 | B1 | 10/2002 | Garcia | |
| 6,464,389 | B1 | 10/2002 | Ghoorahoo | |
| 6,478,195 | B2 | 11/2002 | Duquet | |
| 6,510,965 | B1 | 1/2003 | Decottignies | |
| 6,644,513 | B1 | 11/2003 | Nesbitt | |
| 6,814,265 | B2 | 11/2004 | Clifford | |
| 6,990,047 | B1 | 1/2006 | Barbagiovanni | |
| 6,996,869 | B2 | 2/2006 | Lancette | |
| 7,073,729 | B2 * | 7/2006 | Putz | A44C 15/002 239/326 |
| 7,135,011 | B2 | 11/2006 | Powers | |
| 7,359,287 | B2 | 4/2008 | Baroche | |
| 7,433,275 | B2 | 10/2008 | Ellner | |
| 7,438,873 | B2 | 10/2008 | Saxon | |
| 8,313,009 | B2 | 11/2012 | Parisi | |
| 8,336,790 | B2 | 12/2012 | Kolins | |
| 8,430,262 | B2 | 4/2013 | Corbett | |
| 8,757,443 | B2 * | 6/2014 | Pelfrey | B65D 51/248 222/113 |
| 8,857,663 | B2 | 10/2014 | Scholvinck | |
| 8,875,929 | B1 | 11/2014 | Forney | |
| 8,947,382 | B2 | 2/2015 | Winkler | |
| 8,988,349 | B2 | 3/2015 | Alberth | |
| 9,089,190 | B2 | 7/2015 | Booker | |
| 9,347,749 | B2 | 5/2016 | Olah | |
| 2003/0116587 | A1 | 6/2003 | Garcia | |
| 2004/0000566 | A1 * | 1/2004 | Lowry | A47K 5/122 222/184 |
| 2004/0065700 | A1 | 4/2004 | Milian | |
| 2004/0071048 | A1 | 4/2004 | Ellner | |
| 2004/0144811 | A1 | 7/2004 | Pennaneac'h | |
| 2005/0022554 | A1 | 2/2005 | Davidson | |
| 2005/0242137 | A1 | 11/2005 | Fishman | |
| 2006/0091156 | A1 | 5/2006 | Powers | |
| 2006/0126444 | A1 * | 6/2006 | Ellner | G04B 37/127 368/246 |
| 2006/0138179 | A1 * | 6/2006 | Suffa | B65D 47/0804 222/490 |
| 2007/0023453 | A1 | 2/2007 | Simkins | |
| 2008/0029548 | A1 | 2/2008 | De Wree | |
| 2008/0178977 | A1 | 7/2008 | Nauman | |
| 2008/0230560 | A1 | 9/2008 | Powers | |
| 2008/0245104 | A1 * | 10/2008 | Steele | A44C 5/003 63/1.12 |
| 2008/0251539 | A1 | 10/2008 | Yapaola | |
| 2009/0134184 | A1 | 5/2009 | Stollmann | |
| 2009/0302064 | A1 | 12/2009 | Lavabre | |
| 2010/0001025 | A1 | 1/2010 | McCormick | |
| 2010/0084432 | A1 | 4/2010 | Pelfrey | |
| 2011/0127293 | A1 | 6/2011 | Pascatore | |
| 2011/0139823 | A1 | 6/2011 | Staudt | |
| 2011/0155765 | A1 | 6/2011 | Properzi | |
| 2011/0220652 | A1 | 9/2011 | Corbett | |
| 2012/0085782 | A1 | 4/2012 | Futori | |
| 2012/0114800 | A1 * | 5/2012 | McKay | A23L 2/52 426/72 |
| 2012/0138637 | A1 | 6/2012 | Ciavarella | |
| 2012/0168461 | A1 | 7/2012 | Topits | |
| 2012/0282011 | A1 | 11/2012 | Francois | |
| 2013/0058704 | A1 | 3/2013 | Yamada | |
| 2013/0086943 | A1 | 4/2013 | Turney | |
| 2014/0158793 | A1 | 6/2014 | Sims, Sr. | |
| 2014/0252032 | A1 | 9/2014 | Corbett | |
| 2015/0024085 | A1 | 1/2015 | McBean | |
| 2015/0158042 | A1 | 6/2015 | Parker | |
| 2015/0216367 | A1 | 8/2015 | Barbier | |
| 2016/0044997 | A1 | 2/2016 | Horgan | |
| 2017/0216519 | A1 * | 8/2017 | Vouillamoz | A44C 15/002 |
| 2017/0295893 | A1 * | 10/2017 | D'Alessandro | A44C 15/002 |

* cited by examiner

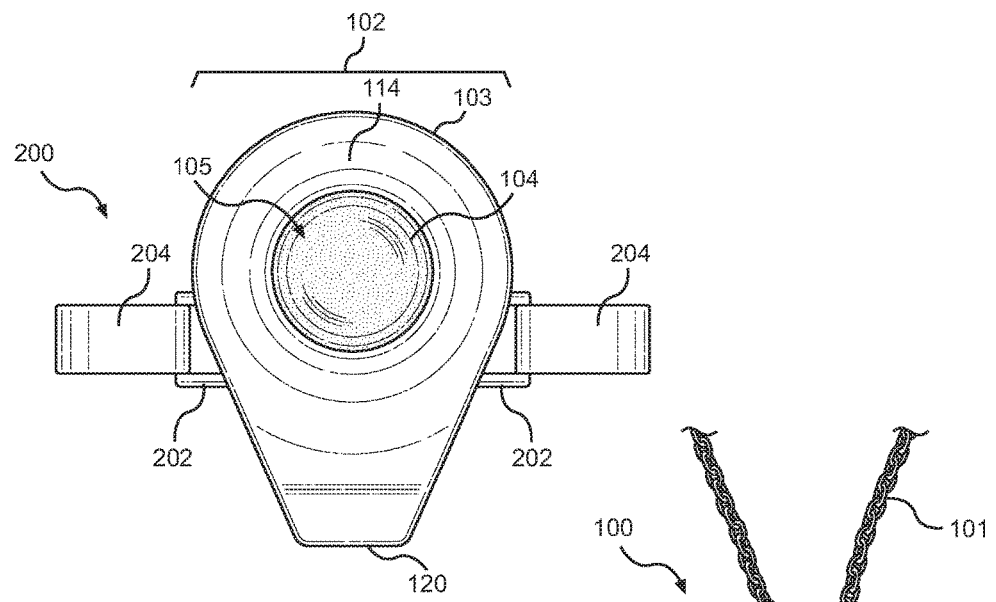
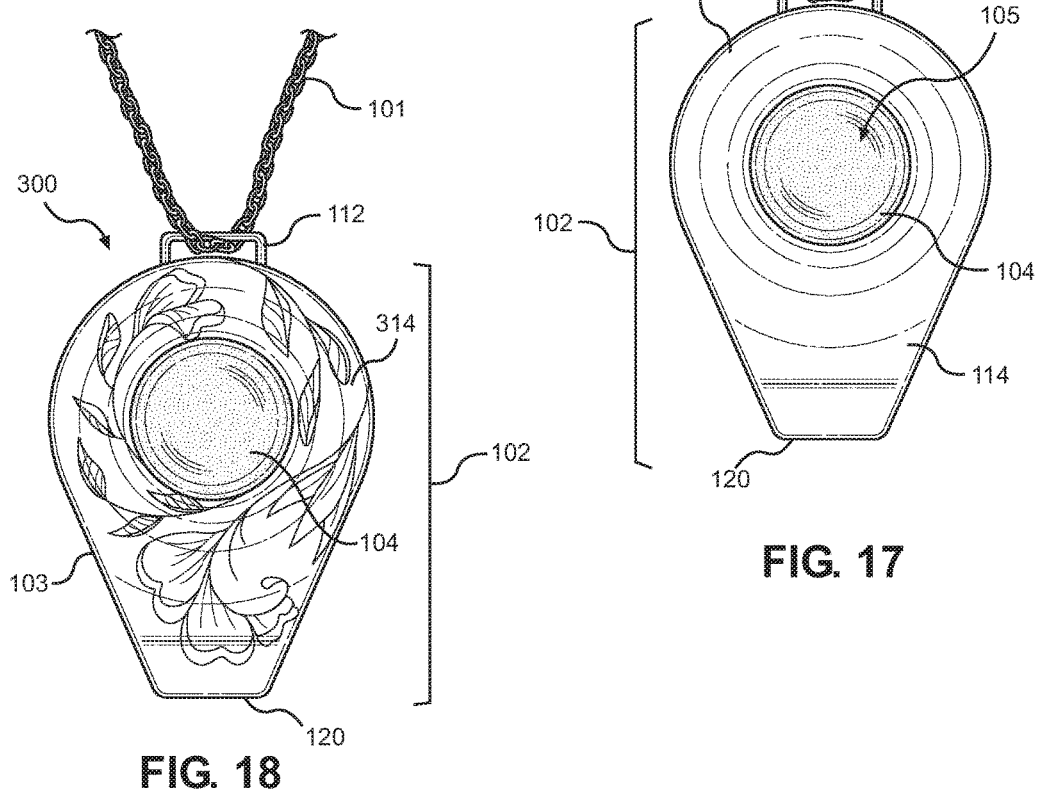
FIG. 16
FIG. 17
FIG. 18

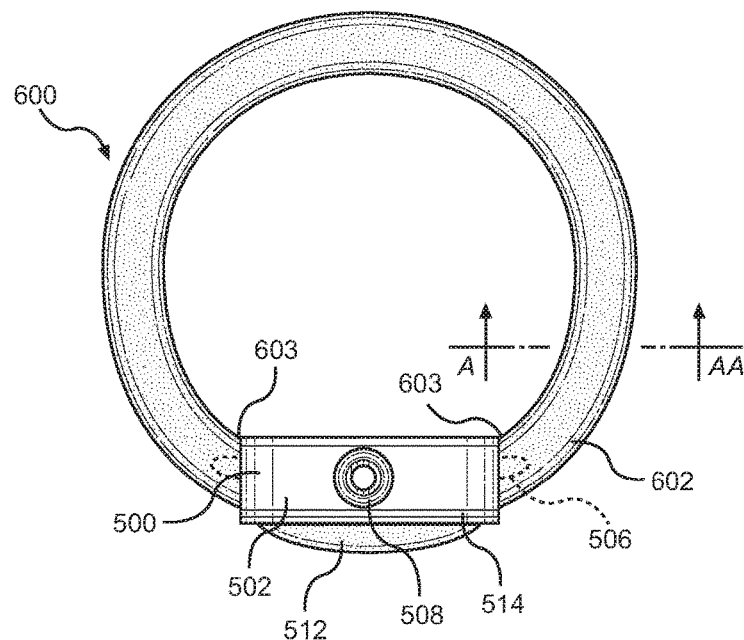
FIG. 26
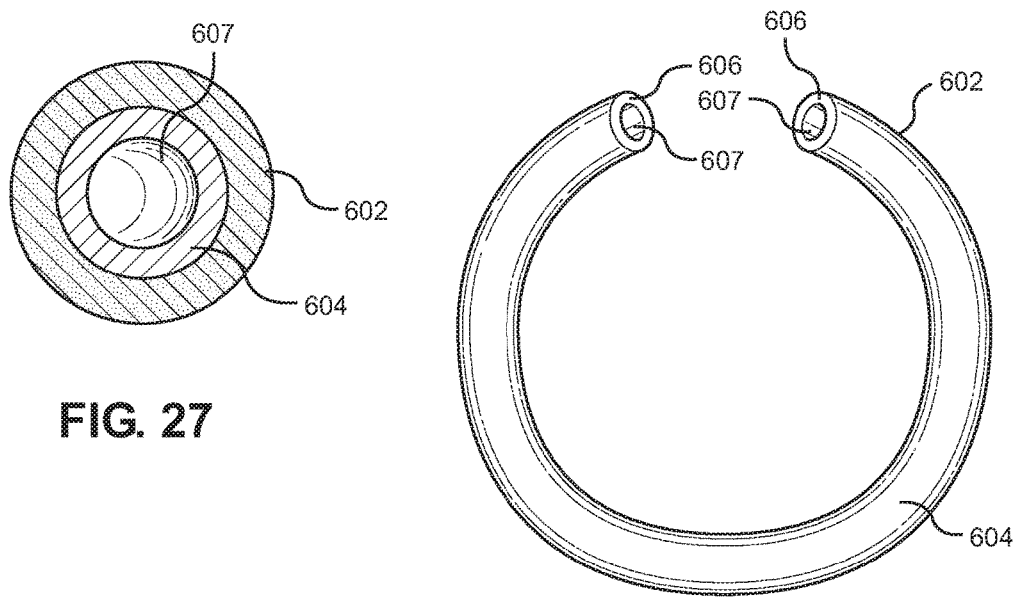
FIG. 27
FIG. 28

LIQUID DISPENSER DEVICE THAT CAN BE WORN AS JEWELRY

RELATED APPLICATION

This application is a Continuation-In-Part Application of, and claims the benefit of priority to, the U.S. patent application for "Liquid Dispenser Device That Can Be Worn As Jewelry", Ser. No. 14/556,548, filed on Dec. 1, 2014, and currently co-pending, which in turn claims the benefit of priority to, the U.S. Provisional Patent Application, Ser. No. 61/913,377, filed on Dec. 8, 2013.

FIELD OF INVENTION

The present invention relates generally to the field of liquid dispensers. More specifically, the present invention pertains to a device that quickly dispenses a stored liquid that is also wearable as an item of jewelry. The present invention is particularly, though not exclusively, useful as a liquid hand sanitizer dispenser worn as jewelry.

BACKGROUND

According to some estimates, up to 80 percent of all infections are spread by hands. The Center for Disease Control and Prevention states the most important way to prevent the transmission of bacteria and dangerous diseases is to wash hands frequently with soap and water. However, when soap and water are unavailable, the Center for Disease Control and Prevention recommends the use of alcohol-based hand sanitizers, which, when used correctly, kill 99.9 percent of germs within 30 seconds after application.

Liquid alcohol-based hand sanitizers work by destroying the outer protein layer of viruses and bacteria, effectively rendering the pathogens ineffective. Although hand sanitizers were invented in the 1960s, they did not gain popularity until the late 1990s when viral outbreaks such as the H1N1 flu virus led to concern regarding sanitation in public areas. Thus, prior to the last decade, hand sanitizers were typically found mostly in clinical and food service settings. Now hand sanitizers are prevalent in households, grocery stores, office buildings, and other public facilities.

Dispensers for soap, lotion, and skin care products are well known. Most individuals encounter liquid dispensers for hand sanitizers, as well as other liquids including soap, lotion, and skin care products, multiple times throughout their daily routine. These dispensers come in various forms such as wall mounts, bottles, bags, and tubes. They are dispensed in various ways and may be refilled after being exhausted and others are simply disposed of once exhausted. Some liquid dispensers utilize sensors to dispense liquids, while others require manual operation by, for example, squeezing a tube or compressing a pump. The liquid is contained inside of these dispensers and can be refilled by bags, cartridges, tubes, or manually refilling from one dispenser to another. The liquid within the bottles, bags, and tube dispensers are usually engaged by using one's hand to squeeze, shake, or pour the liquid into one's hand for use.

The liquid dispensers can be found on walls, on surfaces such as counters or desks, and carried inside personal carriers such as backpacks purses, messenger bags, and briefcases. They may also be attached to personal carriers such as backpacks, purses, messenger bags, and briefcases. They may also be attached to personal carriers by a ring, hook, clip, or band.

It is common for hand sanitizer dispensers to be located on desks, mounted on walls, or otherwise located in visible areas where their use would be most beneficial. The wall mounted dispensers generally use a collapsible bag that contains the liquid. The bag has an attached compact fluid pump or valve. The bag is simply placed in the dispenser with the compact fluid pump or valve properly seated where it will project or expel the liquid from the bag. Liquid is dispensed onto the hand by a hand-operated lever which depresses and activates the compact fluid pump or valve. Examples of this can be seen in U.S. Pat. No. 6,216,916 and other variations of the general theme. The prior art referred to and other prior art well known to those versed in this art know that these wall mount dispensers are of standard size and are confined to walls in bathrooms, washrooms, and throughout public facilities.

The physical presence of a wall mounted hand sanitizer dispenser serves as a visual reminder for employees, patrons, or habitants of a home to utilize the wall mounted hand sanitizer dispenser to limit the spread of bacteria and viruses.

In stark contrast, portable hand sanitizer dispensers located within a purse, messenger bag, backpack, or even in the user's pocket cannot serve as a visual reminder to use the hand sanitizer and may cause users to forget to use a hand sanitizer liquid when it would be the most beneficial to do so. Typical portable dispensers are in the form of bottles, bags, and tubes and often are confined to locations such as personal carriers, pockets, drawers, and surfaces.

In addition to the lack of a visual reminder, small portable hand sanitizer dispensers are also not immediately available to a user for quick access and instead require the individual to look through their purse, bag, backpack, etc., in order to locate the portable dispenser. In certain situations, not having quick and easy access to hand sanitizer fluid from a portable dispenser is problematic. For example, police officers who frequently encounter multiple individuals and locations have a need to sanitize their hands quickly and frequently. For those police officers, attempting to find a hand sanitizer portable dispenser located in a bag or police car is cumbersome and time consuming. Teachers, nurses, food service providers and numerous other professionals have a similar need for quick and frequent access to a hand sanitizer portable dispenser. The lack of quick and easy access to a hand sanitizer results in less frequent use of a hand sanitizer than would ordinarily be desired.

Additionally, the mere act of gaining access to a hand sanitizer portable dispenser stored in a purse or pocket would risk transmitting any germs located on the user's hands to that stored location. For example, an individual who touched a contaminated surface and desired to use a hand sanitizer portable dispenser stored in her purse to sanitize her hands likely will use her contaminated hands to reach into the purse to retrieve the hand sanitizer dispenser, thus contaminating the interior of the purse.

Even once retrieved, conventional portable dispensers containing hand sanitizers and other liquids typically require the removal of a cap or lid in order to dispense the liquid. These caps or lids are typically required to minimize the possibility that the liquid hand sanitizer could spill or leak into a user's backpack, purse, pocket, etc. Therefore, a user with contaminated hands risks cross contaminating the cap or lid when attempting to use a conventional portable hand sanitizer dispenser. If the cap is simply discarded, conventional dispensers will simply leak and risk damage to their exposed dispensing components. After sanitizing their hands, a user must again touch the cross-contaminated cap or lid in order to close the same defeating the entire purpose of sanitizing their hands in the first place.

Should a user wish to avoid cross-contaminating their purse, bag or pocket, the user cannot easily wear conventional portable hand sanitizer dispensers. Moreover, the mere act of wearing a conventional portable hand sanitizer in the form of a bottle or tube might subject the user to possible ridicule in certain work or social environments, as most of these portable dispensers are not functional as outerwear or aesthetically pleasing.

In light of the foregoing, there is a need for a portable liquid dispenser that reduces the likelihood of cross-contamination, is quickly accessible, and serves as a visual reminder to apply hand sanitizer more frequently.

SUMMARY OF THE INVENTION

The present invention is directed at a liquid dispenser that can be worn as jewelry. The liquid dispenser disclosed herein is configured to be worn on one's person, is readily available for use and is aesthetically pleasing. The present invention protects the liquid dispensing components to minimize leaking while avoiding the need for a cumbersome and easily lost cap or lid.

In several embodiments, the liquid dispenser includes an outer shell enclosing an internal bladder assembly with a valve that dispenses liquid through the outer shell. The outer shell has one or more attachment brackets used to connect the outer shell to other devices such as a necklace, bracelet or strap that enables a user to wear the dispenser. Numerous attachment brackets of various geometries and structures are known in the art and include bails for use with necklaces or lugs for use with watches.

The bladder assembly has a flexible bladder in fluid communication with a valve with an opening tip. The valve is connected to the flexible bladder by a neck. Fluid, such as hand sanitizer, is stored within the flexible bladder. The flexible bladder can be made of various materials including, but not limited to, plastic, silicone, or rubber. Fluid is released from the opening tip of the valve when the flexible bladder is compressed sufficiently to open the tip of the valve. When compression of the flexible bladder ceases, the tip of the valve closes and re-seals the flexible bladder. The tip of the valve opens and closes by way of a flexible slit. The outer shell has an access to enable a user to access the internal bladder in order to compress the flexible bladder and release a controlled amount of fluid. The outer shell is made up of at least two parts forming an interior volume to house the bladder assembly.

In one embodiment of the liquid dispenser that can be worn as jewelry, the outer shell is made of an anterior half and a posterior half that are connected to one another by a hinge. In this embodiment, the access is provided by a single opening through the outer shell to expose a portion of the flexible bladder housed within. The opening can be various shapes and sizes, but is large enough to allow a finger to have access to the bladder assembly to operate the device. The outer shell is configured as a truncated teardrop shape terminating in a flat surface with an aperture housing the tip of the valve and allowing fluid to exit the outer shell. A single attachment bracket formed into a bail is connected to the outer shell opposite the flat surface. The term "bail" is commonly used to describe the component of a pendent used to attach or hang a pendant on a chain, strap, sting, etc. To form a pendant, a necklace is attached to the bail to enable a user to wear the outer shell and enclosed bladder assembly as a pendent. The outer shell can be made of various materials including, but not limited to, rubber, silicone, plastic, or precious metals. The outer shell can be various shapes, sizes, and colors depending on the desired use or aesthetic preference of the user. In addition, the outer shell can be coated or decorated with various materials including, but not limited to, gems, enamel of various colors and designs, and rhinestones.

In another embodiment of the liquid dispenser that can be worn as jewelry, the outer shell is made up of a receptacle and a watch face connected together by a hinge and enclosing the flexible bladder. Two attachment brackets formed into lugs are connected to the receptacle opposite one another. A "lug" is commonly used to describe the protrusion from the case of a wristwatch to which the strap or bracelet attaches. Watch straps are connected to the lugs to enable a user to wear the liquid dispenser as a wrist watch. Formed into the receptacle is an opening where the neck of the flexible bladder is positioned so that the valve of the bladder assembly is located outside of the receptacle. The receptacle has an opening housing the tip of the valve and allowing fluid to exit the outer shell. The watch face can be made of a flexible material to allow a user to access the flexible bladder by simply pressing on the watch face, which in turn will compress the flexible bladder. Alternatively, the watch face can be opened about the hinge to provide access to the flexible bladder for use.

In another embodiment of the liquid dispenser that can be worn as jewelry, liquid is stored in a circular pump/valve device that is attached to a flexible silicone tube enclosing a liquid container. The pump/valve device consists of a circular base, flexible dome, and a retaining ring. The flexible dome is placed on the circular base and secured with the retaining ring. Although the pump/valve device is described as circular, it is not limited to a circular shape and can be various shapes and sizes depending on the use or the aesthetics of the user.

The circular base has two connectors positioned on opposite sides of the outer wall of the circular base. The two connectors attach to opposite ends of a liquid container that is enclosed within the flexible silicone tube. In this embodiment, the flexible silicone tube is worn around the wrist as a bracelet or necklace. The flexible tube can be formed from various materials and can be various lengths, colors, and designs. At a 90 degree angle to the two connectors is a spring-loaded ball check valve. However, other valves can also be used. When the pump/valve device is not in use, the ball of the ball check valve acts as a closing member, which blocks the flow of liquid. When pressure is applied to the flexible dome the pressure pushes the ball, thus contracting the spring and allowing forward flow of liquid to be dispensed through the valve.

In another embodiment of the Liquid Dispenser That Can Be Worn As Jewelry, a detachable face is attached to a silicone jewelry base, enclosing the pump/valve device within the silicone jewelry assembly. The silicone jewelry assembly consists of a silicone base that receives the pump/valve device and is connected to a hollow silicone band. The hollow silicone band encloses the liquid container. When the pump/valve device is placed in the silicone base, a detachable face is attached and covers the flexible dome of the pump/valve device. The detachable face can be a watch face (digital or analog) or have a design or insignia depending on the use or the aesthetics of the user. The silicone jewelry base can be made of alternative materials including, but not limited to, rubber, plastic, or precious metals. This embodiment of the invention can be configured into a plurality of jewelry options including, but not limited to, a watch, necklace, or bracelet.

When in operation the jewelry will be worn on a patron in its normal manner. Upon the need to use the liquid the patron will simply depress the detachable face of the jewelry which then activates the pump/valve device and administers (dispenses) the liquid from the liquid bags formed into hollow bands into the patron's hand for use.

In another embodiment of the invention, the valve receiver in the outer shell is made up of a first support rib formed with a first semi-circular opening and a second support rib formed with a second semi-circular opening formed in both the anterior half and posterior half of the outer shell. The first and second semi-circular openings are sized to receive and secure a valve within the outer shell such that the opening tip of the valve is centered with the aperture of the outer shell and also such that the valve is housed within the shell at a setback distance from the aperture of the outer shell. The setback distance is crucial to ensure that the opening tip of the valve remains at all times within the outer shell, whether open or closed. Preferably, the valve receiver retains the opening tip of the valve at a setback distance from the aperture of the outer shell even when the valve is at an open position. Such a configuration ensures that the delicate features of the opening tip of the valve at all times are protected from inadvertent contact by the user and eliminates the need for a cap.

An alternative embodiment of the bladder assembly works in combination with the first and second rib embodiment of the valve receiver wherein the bladder assembly has a flexible bladder formed with a retention bulb and neck. A sleeve is slidably fitted onto the neck and is preferably formed with a retention groove. An alternative cross-slit valve is formed with a retention ring opposite the opening tip of the valve such that the retention ring of the valve fits in the retention groove of the sleeve. The sleeve is permanently bonded to the neck of the flexible bladder through any known means in the art, such as sonic welding. Once the sleeve is bonded to the neck of the flexible bladder, the valve may be removably attached to the sleeve. Nothing in this embodiment excludes the use of a single slit valve as opposed to a cross-slit valve, provided the valve is fitted with the retention ring opposite the opening tip of the valve. The retention bulb of the flexible bladder is sized to fit against the second support rib to prevent lateral movement of the valve with respect to the outer shell such that the setback distance is preserved at all times during use.

In use, a user simply has to compress the flexible bladder through the opening access in the anterior half of the outer shell thereby dispensing sanitizing liquid from the bladder, through the valve and out the aperture of the outer shell.

BRIEF DESCRIPTION OF THE DRAWINGS

The nature, objects, and advantages of the present invention will become more apparent to those skilled in the art after considering the following detailed description in connection with the accompanying drawings, in which like reference numerals designate like parts throughout, and wherein:

FIG. 16 is a front view of an alternative embodiment of the dispenser of the present invention, showing the dispenser configured with two bails located on each side of the outer shell case with a strap attached to each bail;

FIG. 17 is a front view of the dispenser of the present invention, showing a necklace with a dispenser attached to a necklace;

FIG. 18 is a front view of an alternative embodiment of the dispenser of the present invention, showing a necklace with a dispenser with a decorative overlay and hanging on a necklace by a bail;

FIG. 26 is a perspective side view of a watch or bracelet constructed in accordance with the alternative embodiment pump/valve device of the present invention shown in FIGS. 23 through 25, and showing a silicone band and pump/valve device and valve;

FIG. 27 is the cross-sectional view of the silicone band taken at line A-AA of FIG. 26, showing the enclosed liquid container;

FIG. 28 is an isometric view of the liquid container of the alternative embodiment of the silicon band of the present invention shown in FIGS. 25 through 27, and showing connectors that attach to the first and second connectors of the valve/pump device;

DETAILED DESCRIPTION OF A THE INVENTION

Throughout, the term "liquid" will be used to describe the product being dispensed, understanding various skin care products and dispensable products may be used with this jewelry. This includes, but is not limited to, hand sanitizer, perfume, soap, skin care products, make-up, sunscreen, etc.

Figure 1:
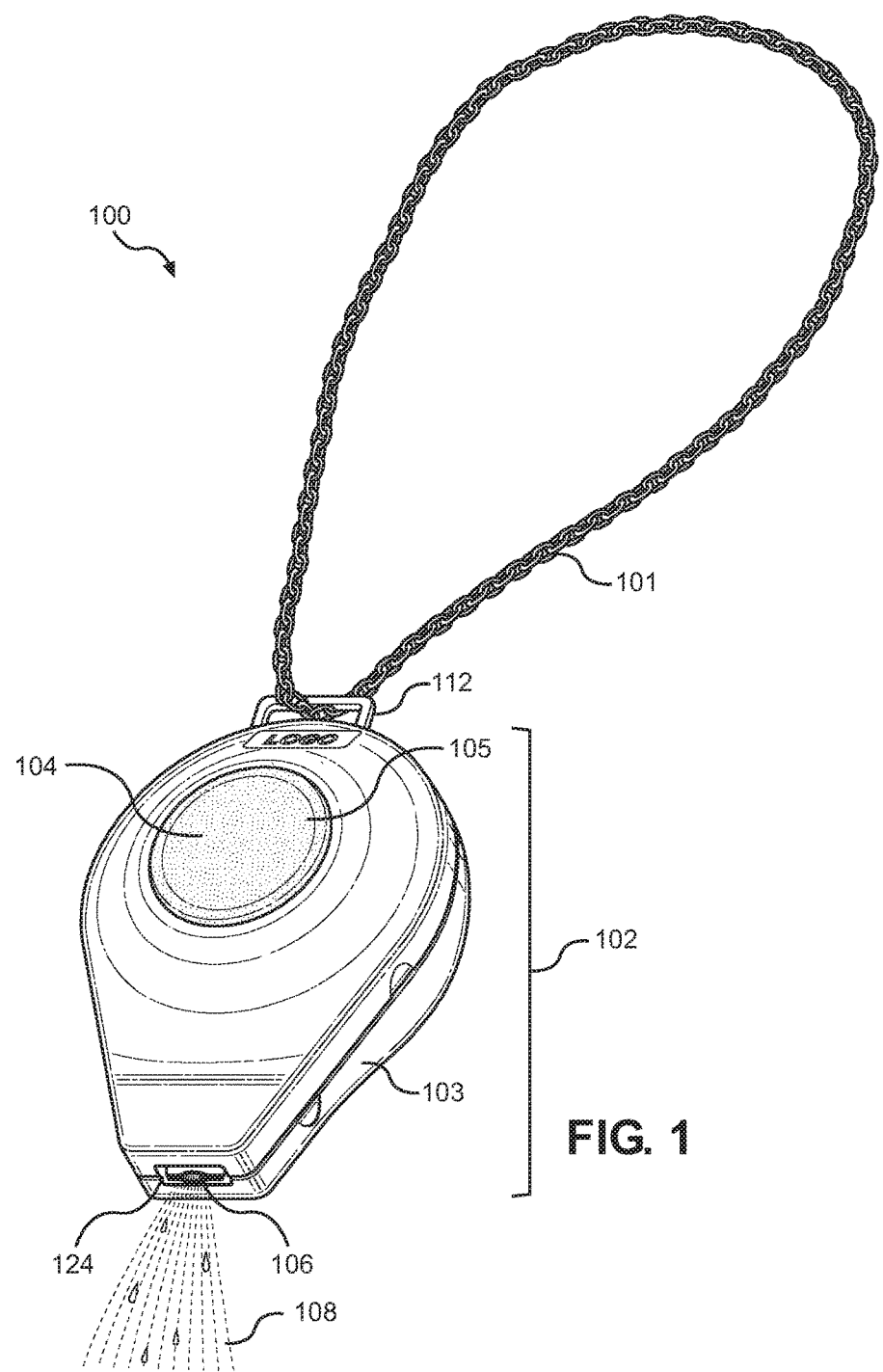
FIG. 1 is a perspective view of the present invention, showing a chain necklace with a dispenser attached to the necklace and dispensing liquid.

Referring initially to FIG. 1, a preferred embodiment of the Liquid Dispenser That Can Be Worn As Jewelry of the present invention is shown and generally designated 100. The Liquid Dispenser That Can Be Worn As Jewelry 100 consists of a necklace 101 and a dispenser 102, which dispenses liquid 108. The dispenser 102 comprises a bail 112, bladder assembly 105, and an outer shell 103. The bladder assembly 105 consists of a flexible bladder 104 with a neck (not shown) and a valve (not shown) which ends in a flexible slit 106. The flexible slit 106 is exposed through rectangular aperture 124 and dispenses liquid 108.

Necklace 101 can be any length depending on the use or the general aesthetics of the user of the Liquid Dispenser That Can Be Worn As Jewelry 100 of the present invention. In FIG. 1, the necklace 101 is shown as a chain necklace 101. However, the necklace can be made of different materials known in the art including, but not limited to chain, chord, string, or beads.

The bail 112 is an attachment to the outer shell 103 that allows the dispenser 102, to hang on the necklace 101. Although the bail 112 is depicted in FIG. 1 as rectangular, the bail 112 can be any shape, size, or design, and occupy different locations on the outer shell 103, so long as the bail 112 allows dispenser 102 to hang or attach to necklace 101. In addition, multiple bails 112 may be used, as subsequently discussed in alternative embodiments.

In FIGS. 2-8, the outer shell 103 of the dispenser 102 of the Liquid Dispenser That Can Be Worn As Jewelry 100 of the present invention is shown. Looking first at FIG. 2, the outer shell 103 is shown as a truncated teardrop shape, with a flat surface 120 where the tapered point of a teardrop would normally be located. Although the outer shell 103 is depicted with this shape, the outer shell 103 can be various shapes and sizes, including, but not limited to, heart-shaped, circular, oblong, or triangular. In addition, the outer shell 103 can be coated or decorated with various materials including, but not limited to, gems, enamel of various colors and designs, and rhinestones to provide a variety of aesthetic alternatives.

Figures 2, 3:
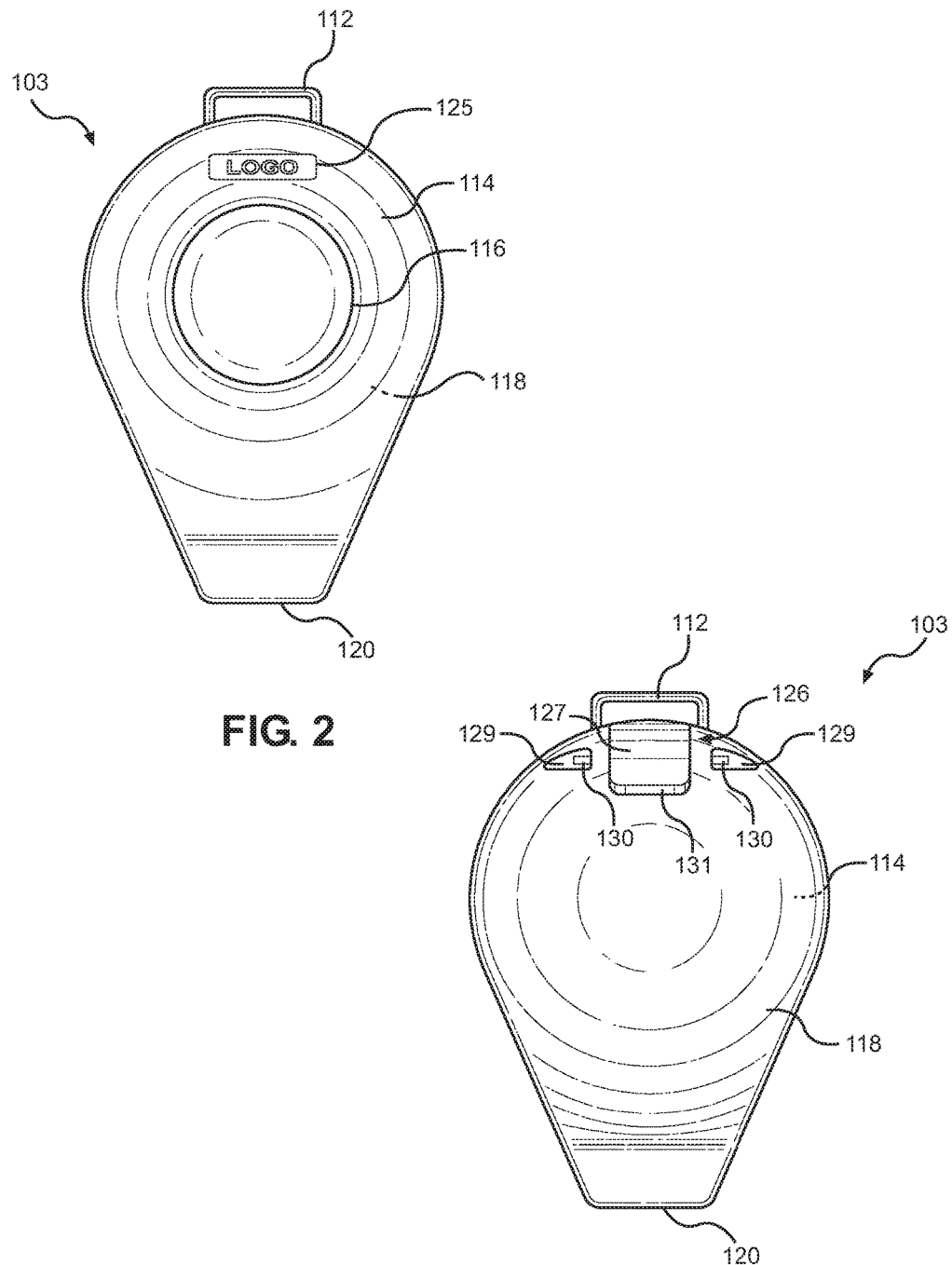
FIG. 2 is a front view of the anterior of the outer shell of the dispenser of the present invention, showing a circular opening through which the flexible bladder (not shown) can be accessed, and an attachment bracket formed into a bail.
FIG. 3 is a back view of the posterior of the outer shell of the dispenser of the present invention, showing the posterior half with no circular opening and a bail.
Figure 8:
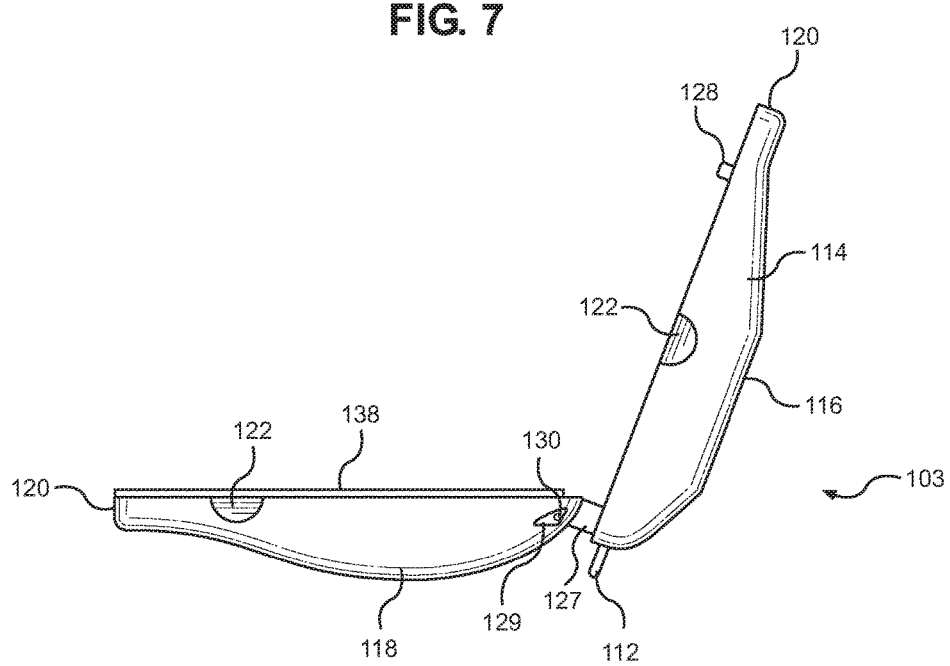
FIG. 8 is a side view of the outer shell of the dispenser of the present invention in the open configuration, showing the anterior and posterior halves, opening indentations, bail, hinge, latch pin, and interior alignment ridge A.

The outer shell 103 is formed with two (2) halves, an anterior half 114 and posterior half 118 (shown in FIG. 2 with dashed lines), which are connected via a hinge system 126 (shown in FIGS. 3 and 8). There is an opening 116 located in the anterior half 114. Although depicted in FIG. 2 as a circular opening 116, the opening 116 can have other shapes such as rectangular, diamond, heart shaped, etc. In addition, the size of the opening 116 can vary, so long as a user's finger can be inserted through the opening 116 in order to apply pressure to the flexible bladder 104 (shown in FIGS. 9, 10 and 11) located within the outer shell 103. The anterior half 114 is also shown with a logo 125. The posterior half 118 of the outer shell 103, as depicted in FIG. 3, has no circular opening 116, however it could also be formed with an opening to allow dispensing from either or both sides of the device.

Figure 6:
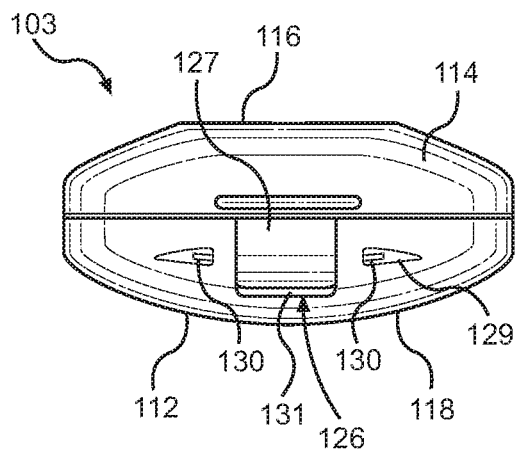
FIG. 6 is a top view of the outer shell of the dispenser of the present invention, showing the bail, hinge, and the two halves of the outer shell in a closed configuration.

FIG. 3 shows the back view of the outer shell 103 and depicts the hinge system 126. The hinge system 126 connects the anterior half 114 and posterior half 118 of outer shell 103 and allows a limited angle of rotation between the two (2) halves. FIG. 6 shows the top view of the outer shell 103 and also shows the hinge system 126, which includes a hinge aperture 131 on the posterior half 118 of the outer shell 103 sized to receive a hinge tab 127 on the anterior half 114 of the outer shell 103. Hinge slots 129 are recessed into the surface of the posterior half 118 of the outer shell to enable a hinge pin 130 to pass through a portion of the posterior half 118 and the hinge tab 127 thereby connecting the posterior half 118 to the anterior half 114. In other variations of the Liquid Dispenser That Can Be Worn As Jewelry 100 the anterior and posterior halves 114 and 118 may completely separate and snap together without the need of a hinge system 126. As stated previously, to open the outer shell 103 and separate the anterior half 114 from the posterior half 118, the user applies pressure to the opening indentations 122 to force the halves to separate, rotating on hinge system 126.

Figure 4:
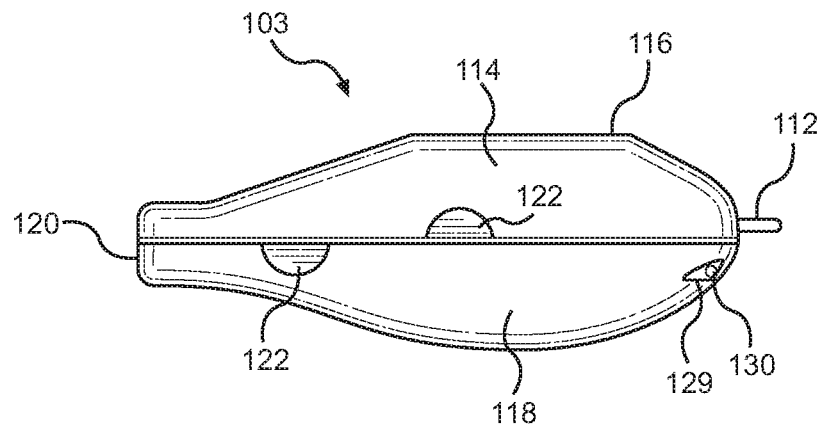
FIG. 4 is a side view of the outer shell of the dispenser of the present invention, showing the division of the two halves of the outer shell in a closed configuration, the bail, and opening indentations.

In FIG. 4, the side view of the outer shell 103 of the Liquid Dispenser That Can Be Worn As Jewelry 100 of the present invention is shown. As stated above, the outer shell 103 consists of two (2) halves, the anterior half 114 and the posterior half 118, which open exposing the interior (not shown) of the outer shell 103. In order to pull apart the two (2) halves, the user uses the opening indentations 122 to open the outer shell 103. Although the mechanism used to open the outer shell 103 is opening indentations 122, other mechanisms can be used, including, but not limited to, clasps, locks, latches, or push-buttons.

Figure 5:
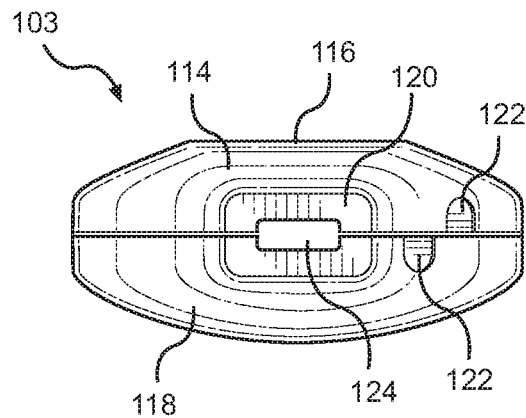
FIG. 5 is a bottom view of the outer shell of the dispenser of the Liquid Dispenser That Can Be Worn As Jewelry of the present invention with the two halves of the outer shell in a closed configuration, and showing the rectangular aperture and opening indentations.

In FIG. 5, the bottom of the outer shell 103 of the Liquid Dispenser That Can Be Worn As Jewelry 100 is shown. The flat surface 120 has a rectangular aperture 124 where the flexible slit 106 (not shown) of valve 150 (not shown) is exposed. Although the aperture 124 is depicted as rectangular, the shape of the aperture 124 may vary depending on the use or aesthetic design of the dispenser 102, valve 150, or the type of valve used.

Figure 7:
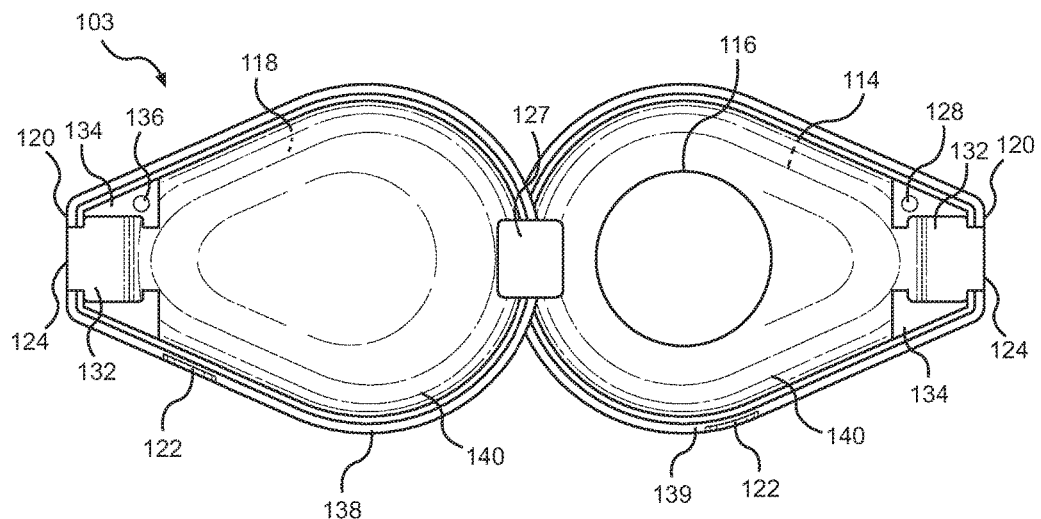
FIG. 7 is a plan view of the outer shell of the of the dispenser of the present invention in the open configuration, showing the interior of the anterior and posterior halves, opening indentations, hinge, circular opening, interior alignment ridge A and B, latch pin, latch receiver, and valve receiver.

FIGS. 7 and 8 show the opened outer shell 103. The interior surface area 140 of the outer shell 103 is hollow to receive the bladder assembly 105 (not shown). At the distal end of each half 114 and 118 of the outer shell 103 is a valve receiver 134, which has a recess 132 shaped to receive the valve 150 (not shown) and neck 148 (not shown) of the bladder assembly 105 (not shown).

In order for the outer shell 103 to remain securely closed during use, interior alignment ridge A 138 and alignment ridge B 139, fit together to keep the anterior and posterior halves 114 and 118 from shifting when closed. In addition, a latch pin 128 on the anterior half 114 of the outer shell 103 is received by latch receiver 136 on the posterior half 118, keeping the outer shell 103 securely closed until opened by the user. FIG. 8 shows the perspective side view of the opened outer shell 103 of the Liquid Dispenser Device That Can Be Worn As Jewelry 100 of the present invention. From this view, the latch pin 128 and alignment ridge A 138 are clearly visible. While a latch pin 128 and latch pin receiver 136 are used to keep the anterior half 114 and posterior half 118 closed, other mechanisms can be used including, but not limited to, clasps, locks, or push-button mechanisms.

Figure 9:
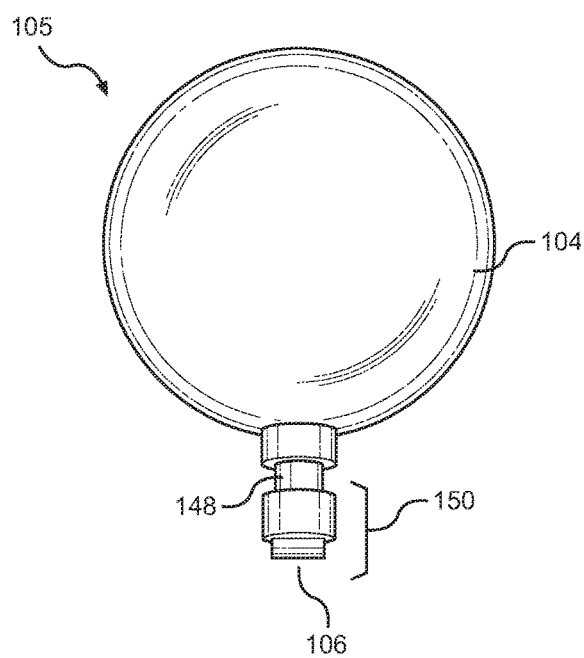
FIG. 9 is a front view of the bladder assembly of the present invention, showing a flexible bladder, neck, and valve.
Figures 10, 11:
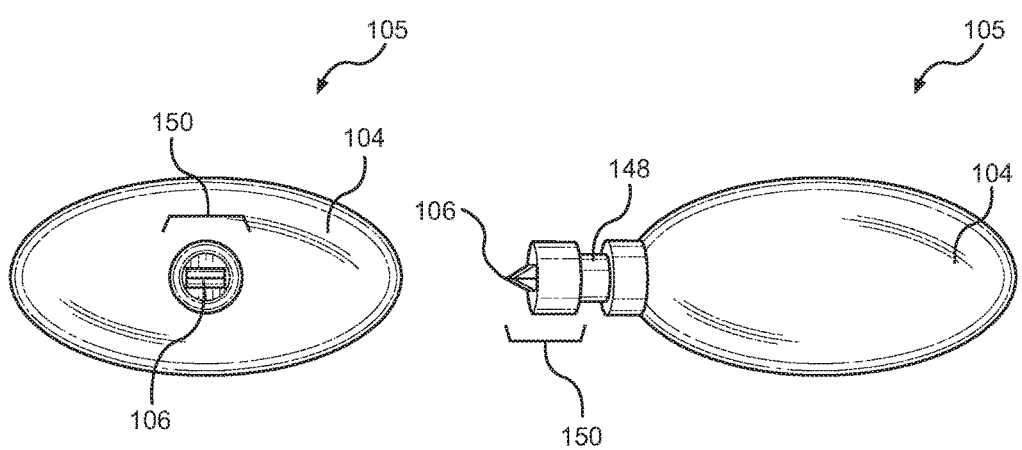
FIG. 10 is a bottom view of the bladder assembly of the present invention, showing the flexible bladder and valve.
FIG. 11 is a side view of the bladder assembly of the present invention, showing the flexible bladder, neck, and valve.

The bladder assembly 105 of the Liquid Dispenser That Can Be Worn As Jewelry 100 is shown in FIGS. 9-11. Looking first at FIG. 9, the bladder assembly 105 consists of three parts: the flexible bladder 104, neck 148, and valve 150.

The flexible bladder 104 is shown in FIGS. 9-11 having an oblate spherical shape, sized to be enclosed by the anterior and posterior halves 114 and 118 of the outer shell 103. The flexible bladder 104 is formed with a neck 148 at one end of the major axis. The flexible bladder may be various shapes and volumes, however, the shape and volume of the flexible bladder 104 corresponds to the size and shape of the outer shell 103. In addition to variations of size and shape, the flexible bladder 104 can be made of rubber, plastic, silicone, or any other material with elastomeric properties. The flexible bladder 104 can also be various colors and designs.

The neck 148 of the bladder assembly 105 is capped with a valve 150, which ends in a flexible slit 106. When in rest, the sides of the flexible slit 106 are closed, stopping liquid 108 (not shown) from exiting the bladder. When force is applied to the flexible bladder 104, the volume of the flexible bladder 104 decreases, and the liquid contained within the flexible bladder 104 is forced through the neck 148, causing the flexible slit 106 of the valve 150 to open, releasing the liquid 108 (not shown). In addition, the bladder assembly 105 of the Liquid Dispenser That Can Be Worn As Jewelry 100 of the present invention is removable, replaceable, and refillable.

Figure 12:
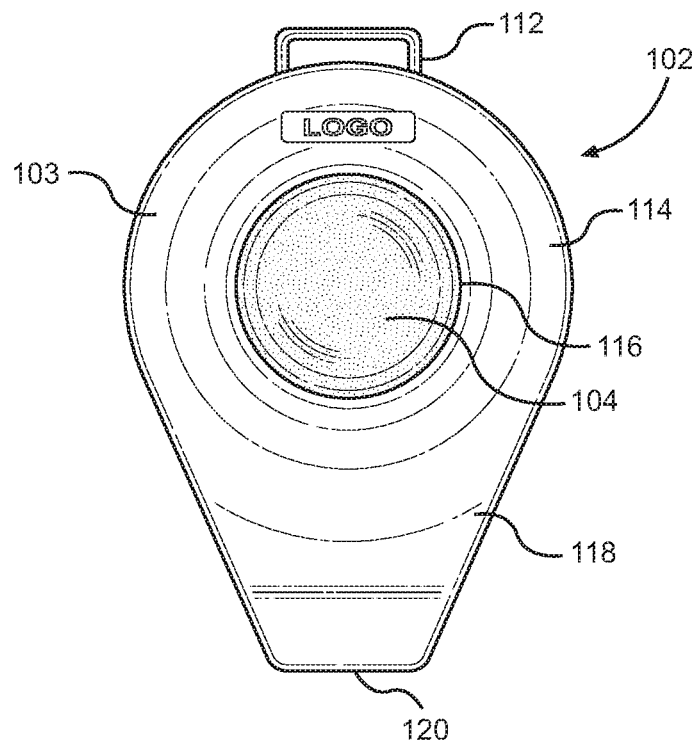
FIG. 12 is a front view of the anterior of the dispenser device of the present invention, showing the bail, outer shell, and the flexible bladder in position within the shell.
Figure 13:
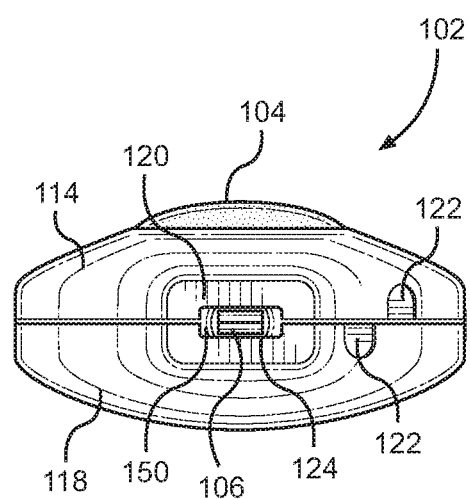
FIG. 13 is a bottom view of the dispenser and valve of the present invention, showing opening indentations, rectangular aperture, valve, and flexible slit.

As shown in FIG. 12, when the bladder assembly 105 is placed within the outer shell 103, flexible bladder 104 is exposed through circular opening 116, as shown in FIG. 12. The flexible slit 106 is exposed through the rectangular aperture 124, as shown in FIG. 13. When operating, the user applies pressure to the portion of the flexible bladder 104 exposed through the circular opening 116.

Figure 14:
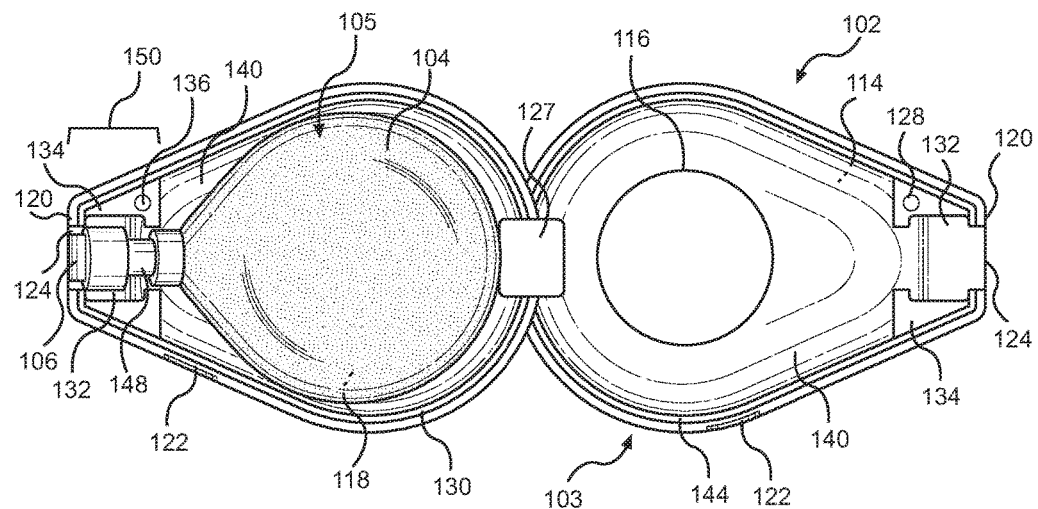
FIG. 14 is a plan view of the dispenser of the present invention in an open configuration, showing the bladder assembly positioned within the outer shell.
Figure 15:
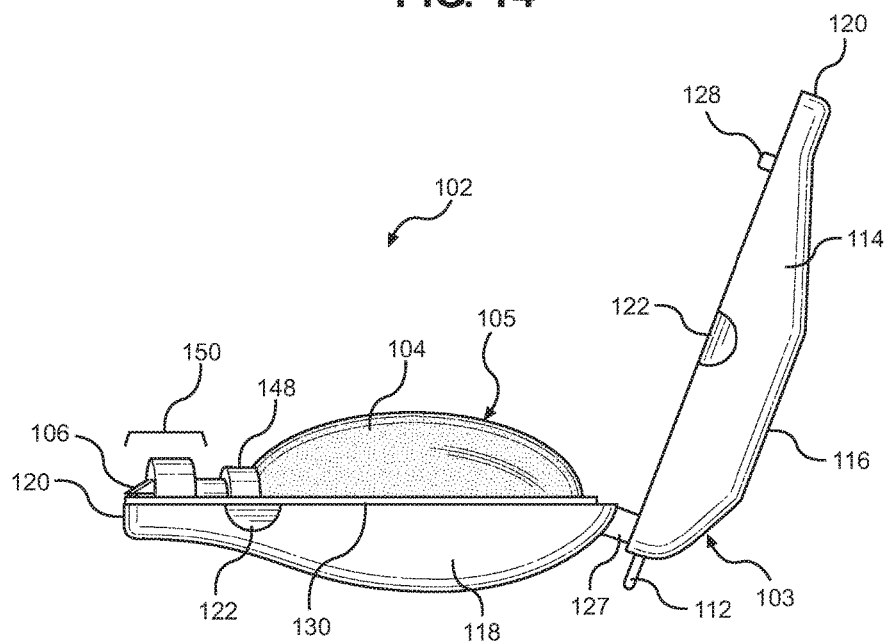
FIG. 15 is a side view of the dispenser of the present invention in an open configuration, showing the bladder assembly positioned within the outer shell.

In FIGS. 14 and 15, the opened dispenser 102 is shown with the bladder assembly 105 placed within the interior surface 140 of the shell case 103. The valve 150 and neck 148 is received by each half of the valve receiver 134, which has a recess 132 shaped to receive the valve 150 and neck 148 of the bladder assembly 105. When closed, the valve receiver 134 holds the valve 150 and neck 148 in place so that liquid (not shown) can be dispensed from the flexible slit 106 through the rectangular aperture 124.

FIG. 16 is an alternative embodiment of the Liquid Dispenser That Can Be Worn As Jewelry of the present invention and generally designated 200. In this embodiment, the hard outer shell 103 is formed with two (2) bails 202, located on the right and left side of the hard outer shell 103. In this embodiment, opposing ends of strap 204 attach to bails 202 to create a bracelet or belt. The strap 204 can be made of silicone, rubber, plastic, any other elastomeric material, or woven material. In addition, strap 204 can be one continuous strap 204, or have a clasp used to attach the ends of two (2) straps 204. Although shown in FIG. 16 as a strap 204, a chain, string, or other material could be used to wear the alternative embodiment of the Liquid Dispenser That Can Be Worn As Jewelry 200 of the present invention around the wrist or waist.

FIG. 17 shows the front view of the preferred embodiment of the Liquid Dispenser That Can Be Worn As Jewelry 100 of the present invention. The dispenser 102 consists of the internal bladder assembly 105, the outer shell 103, and the bail 112. The bail 112 allows the dispenser 102 to hang from the necklace 101. In contrast with FIG. 16, depicting the alternative embodiment of the Liquid Dispenser That Can Be Worn As Jewelry 200, the preferred embodiment of the Liquid Dispenser That Can Be Worn As Jewelry 100 is in the form of a necklace 101, capable of being worn around the neck of the user.

FIG. 18 is an alternative embodiment of the Liquid Dispenser That Can Be Worn As Jewelry of the present invention and generally designated 300. In this embodiment, the outer shell case 103 is coated with a decorative enamel 314. However, as stated previously, the outer shell 103 can be coated or decorated with various materials including, but not limited to, gems, enamel of various colors and designs, and rhinestones. In addition, the outer shell 103 itself can be various colors.

Figure 19:
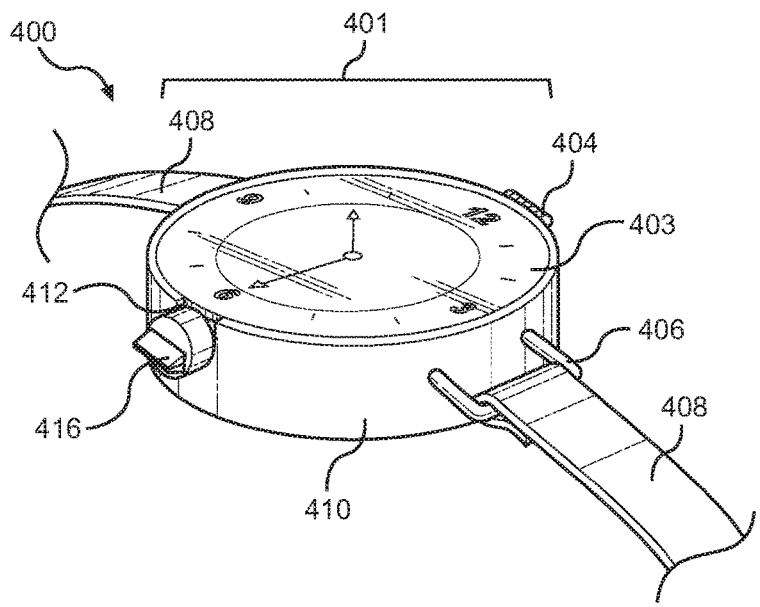
FIG. 19 is perspective view of an alternative embodiment of the dispenser of the present invention, showing a lug, strap, watch base and valve.
Figure 20:
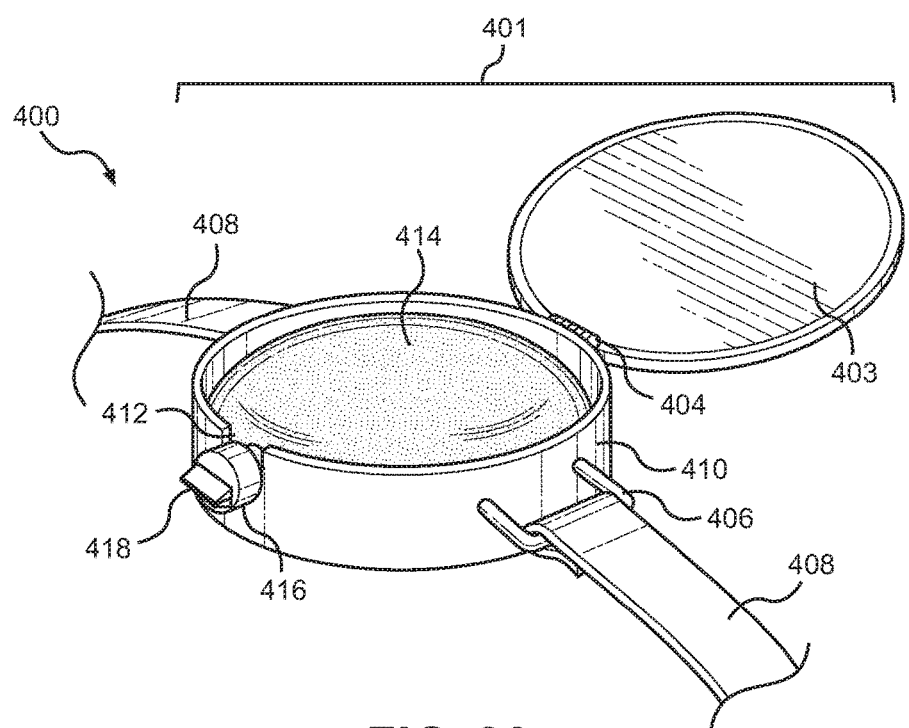
FIG. 20 is a perspective view of the alternative embodiment of the dispenser of the present invention shown in FIG. 19, and showing the opened watch base with the exposed flexible bladder.

In FIGS. 19 and 20, an alternative embodiment of the Liquid Dispenser That Can Be Worn As Jewelry of the present invention is shown and generally designated 400. FIG. 19 depicts a closed and empty watch base 401 with straps 408. The watch base 401 consists of a watch face 403, a receptacle 410, and lugs 406. Lugs 406 allow the watch base 401 to attach to straps 408. The watch base 401 can be made out of various materials including, but not limited to, rubber, plastic, precious metals, or silicone. In addition, the watch base can also be decorated with various materials known to the art including, but not limited to, gems, enamel of various colors and designs, and rhinestones to provide a variety of aesthetic alternatives.

Figure 22:
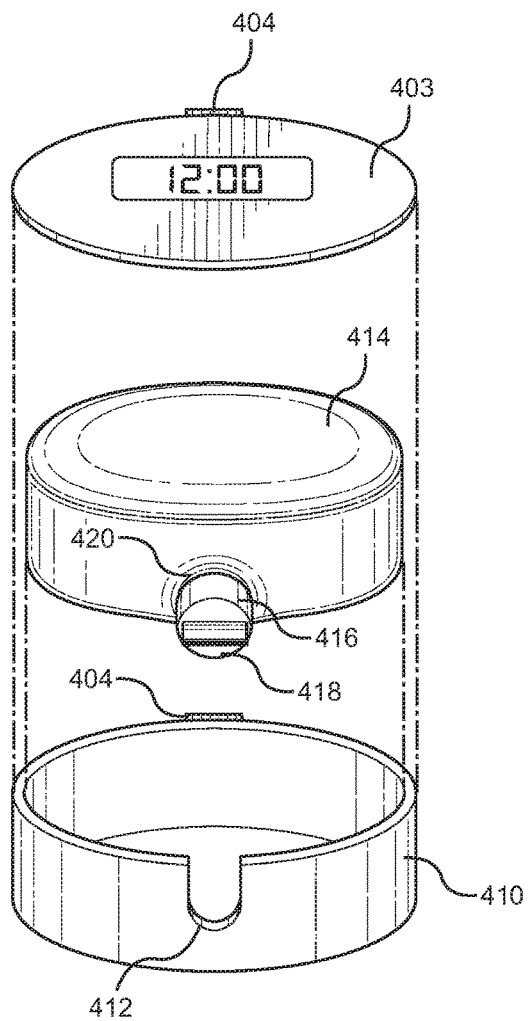
FIG. 22 is an exploded view of the watch base, flexible bladder, and watch face of the alternative embodiment of the dispenser of the present invention shown in FIGS. 19 through 21.

Watch face 403 and receptacle 410 are attached by a hinge 404, which allows the watch face 403 to open, exposing the interior of the receptacle 410, and close again. The watch face 403 can be analog or digital (as shown in FIGS. 19 and 22, respectively) and is flexible, with the ability to compress and decompress into receptacle 410. Although watch face 403 and receptacle 410 are attached by a hinge 404, a variety of different mechanisms known in the art can be used to attach watch face 403 to receptacle 410.

When in use, the watch base 401 receives the flexible bladder 414 (not shown) by placing the flexible bladder 414 (not shown) within the receptacle 410. Formed into the receptacle 410 is an opening 412, where the neck 420 (not shown) of the flexible bladder 414 (not shown) lays when the flexible bladder 414 (not shown) is placed within the receptacle 410. In FIG. 19, the watch face 403 is closed, and thereby acting as a lid to the receptacle 410, enclosing the flexible bladder 414 (not shown) within the receptacle 410.

In contrast, FIG. 20 shows an outer shell configured as a watch base 401 in an open configuration. The flexible bladder 414 is placed within the receptacle 410. As stated above, formed into the receptacle 410 is an opening 412 where the neck 420 (not shown) of the flexible bladder 414 is positioned, causing the valve 416 of the flexible bladder 414 to be positioned outside of the watch base 401. The valve 416 ends in flexible slit 418 where liquid (not shown) is released.

Figure 21:
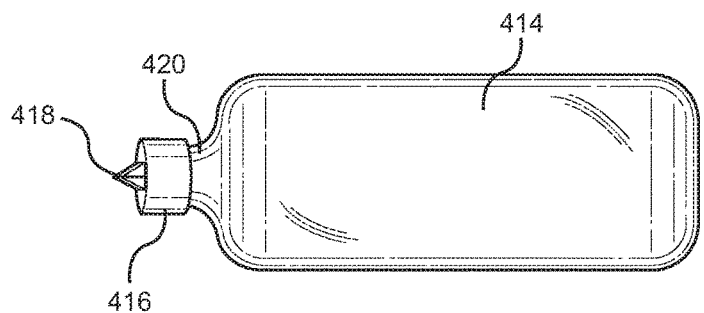
FIG. 21 is the side view of the flexible bladder assembly of the alternative embodiment of the dispenser of the present invention shown in FIGS. 19 and 20, and showing the flexible bladder, neck, and valve.

Looking now at FIG. 21, the side view of the flexible bladder 414 is shown. Here, flexible bladder 414 is shown as cylindrical. However, because the flexible bladder 414 is positioned within the receptacle 410, the shape and volume of the flexible bladder 414 is consistent with the volume and shape of the receptacle 410. Although depicted in FIGS. 19, 20, and 22 as cylindrical, the shape and size of the receptacle 410 can vary. Possible shapes include, but are not limited to, heart-shaped, triangular, diamond, and square. Thus, the flexible bladder 414, can also vary in size and shape.

The flexible bladder 414 is formed with a neck 420. The neck 420 of the flexible bladder 414 is capped with a valve 416, which ends in a flexible slit 418. When no pressure is applied to the flexible bladder 414, the flexible slit 418 of the valve 416 remains in the closed position, not allowing liquid to be dispensed. When pressure is applied to the flexible bladder 414, the flexible slit 418 opens and liquid (not shown) is dispensed. In addition, the valve 416 of the flexible bladder 414 can be removed, allowing the user to refill the flexible bladder 414.

FIG. 22 is an exploded view of the watch face 403, flexible bladder 414, and receptacle 410, showing how the three components fit together as previously discussed. As stated above, flexible bladder 414 is positioned inside the receptacle 410. When positioned within the receptacle 410, the neck 420 of flexible bladder 414 is received by the opening 412 formed into the receptacle 410, resulting in valve 416 to be positioned outside the receptacle 410. Watch face 403 covers the flexible bladder 414 within the receptacle 410, and watch face 403 is attached to receptacle 410 by hinge 404

To operate, the user compresses the watch face 403, which applies pressure to the flexible bladder 414. The pressure applied to the flexible bladder 414 forces liquid (not shown) through the neck 420, causing the flexible slit 418 of the valve 416 to open and release liquid (not shown). When pressure on the flexible bladder 414 is released, flexible slit 418 of the valve 416 closes and the forward flow of liquid (not shown) ceases.

Figure 23:
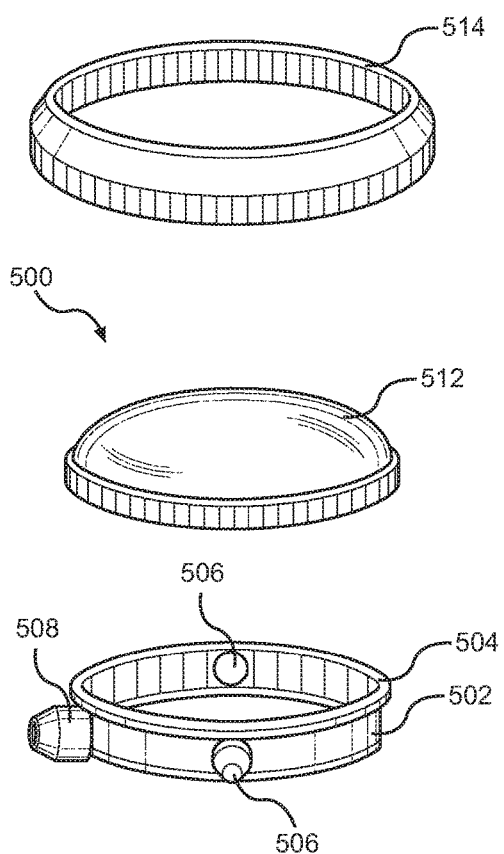
FIG. 23 is an exploded view of the pump/valve device of an alternative embodiment of a dispenser contemplated by the present invention, showing a circular base with a valve, flexible dome, and a retaining ring.

FIG. 23 is another alternative embodiment of the Liquid Dispenser That Can Be Worn As Jewelry of the present invention and having a pump/valve device generally designated 500. FIG. 23 is a perspective side assembly view of the pump/valve device 500. The pump/valve device 500 includes a circular base 504, a circular peripheral wall 502. The circular peripheral wall 502 is the outside surface of the circular base 504. In addition to the circular base 504, the pump/valve device 500 also includes a flexible dome 512, and a retaining ring 514. The flexible dome 512 is positioned on top of the base 504 creating a fluid tight sealed chamber. The flexible dome 512 and base 504 are then secured with a retaining ring 514. It is presented as a circular pump/valve device 500 but may not be limited to that particular shape. The shape and size of the pump/valve device 500 can vary depending on the use or aesthetics of the user. Possible shapes include, but are not limited to, heart shaped, triangular, square, or rectangular.

Figure 24:
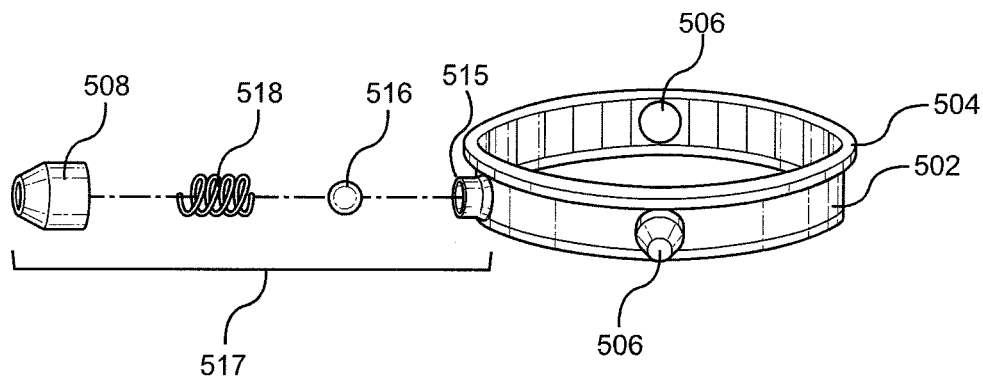
FIG. 24 is an exploded view of a spring-loaded ball check valve to be used in connection with the alternative embodiment of the pump/valve device of the present invention, showing the circular base, valve connector, ball, spring, and valve.

Two connectors 506 extend from the circular peripheral wall 502, this is the location where the liquid containers (not shown) can be attached. FIG. 24 depicts, in an assembly view, a more comprehensive depiction of the mechanism used to dispense the liquid. A third connector 515 extends from the bottom of the circular peripheral wall 502 which connects to a valve 508 that houses a spring 518 that when activated by the depression of the flexible dome 512 (shown in FIG. 23) dispenses liquid (not shown) from the valve 508. More specifically, this embodiment utilizes a spring-loaded ball check valve system 517 that consists of the third connector 515, ball 516, spring 518, and a valve 508. When the pump/valve 500 is not in use, the ball 516 acts as a closing member, which blocks the flow of liquid. When pressure is applied to the flexible dome 512, the pressure pushes the ball 516, thus contracting the spring 518 and allowing forward flow of liquid (not shown) to be dispensed through the valve 508. Although this embodiment is depicted with a spring-loaded ball check valve system 517, any applicable valve may be used.

Figure 25:
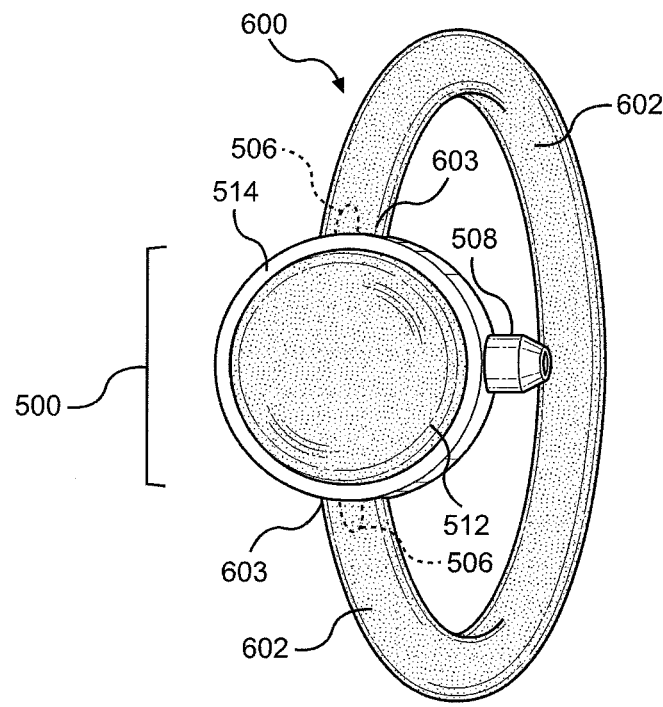
FIG. 25 is a front perspective view of a watch or bracelet constructed in accordance with the alternative embodiment pump/valve device shown in FIGS. 23 and 24 of the present invention, and showing a silicone band connected to the pump/valve device.

FIG. 25 is a front perspective view of a watch or bracelet constructed in accordance with the alternative embodiment of the Liquid Dispenser That Can Be Worn As Jewelry of the present invention. This alternative embodiment is in the form of a watch/bracelet and generally designated 600. The watch/bracelet 600 will be constructed of rubber, silicone, or some other plausible material, colors, and designs. The watch/bracelet bands 602 will be hollow and, as stated above, may be constructed out of any elastomeric material including, but not limited to, rubber, silicone, or plastic. The liquid container (not shown) will be attached to the valve/pump device 500 and enclosed in the hollow watch/bracelet bands 602 of the watch/bracelet 600. FIG. 26 is a side view of FIG. 25. In FIG. 25, the connection of the watch/bracelet band 602 is shown at point 603.

FIG. 27 is a cross-sectional view of the hollow watch/bracelet bands taken at line A-AA of FIG. 26. The liquid container 604 is shown enclosed within the watch/bracelet band 602 along with the hollow interior 607. In addition, FIG. 28 is a side perspective view of band 602 and showing the liquid container 604 that will attach to the first and second connectors 506. There is a liquid container connector 606 at the ends of the liquid container 604 made to fit the first and second connectors 506 of the pump/valve device 500. The liquid container 604 and the watch/bracelet bands 602 are attached to the two connectors 606 at each end of the watch/bracelet bands 602, creating a ring with the watch/bracelet bands 602.

Figure 29:
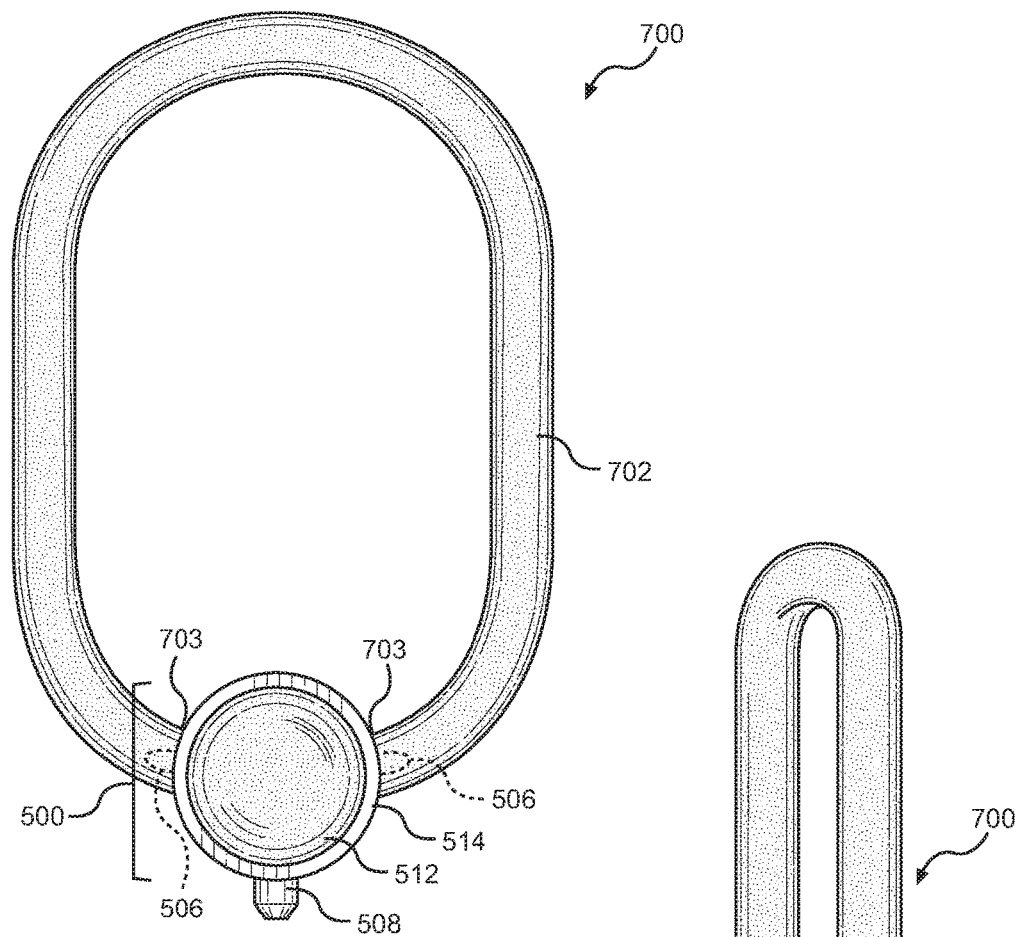
FIG. 29 is a front perspective view of a necklace constructed in accordance with the alternative embodiment of the pump/valve device of the present invention, showing a silicone band and a pump/valve device.

FIG. 29 is a front perspective view of a necklace constructed in accordance with an alternative embodiment of the invention. This alternative embodiment of the Liquid Dispenser That Can Be Worn As Jewelry of the present invention is in the form of a necklace, and generally labeled 700. The necklace 700 will be constructed of rubber, silicone, or some other plausible material of various colors and designs. The hollow bands 702 of the necklace 700 will be hollow and, as stated above, may be constructed out of any elastomeric material including, but not limited to, rubber, silicone, or plastic. Liquid container 704 (not shown) will serve as a liquid bag and is attached to and in fluid communication with the valve/pump 500 by way of connectors 506. The liquid container 704 (not shown) is enclosed in the hollow bands 702 of the necklace 700.

Figure 30:
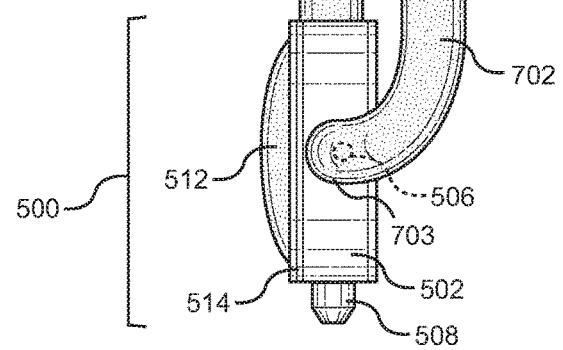
FIG. 30 is a perspective side view of a necklace constructed in accordance with the alternative embodiment of the pump/valve device of the present invention, showing a silicone band and pump/valve device.

FIG. 30 is a side view of FIG. 29. FIG. 29 shows the hollow bands 702 connected to the pump/valve device 500 at point 703. The hollow bands 702 of the necklace have the same structure of the watch/bracket bands 602 shown in FIGS. 27 and 28. The liquid container 704 within hollow bands 702 of the necklace 700, contains a liquid (not shown) and is attached to an in fluid communication with the connectors 506 of the pump/valve device 500.

Figure 31:
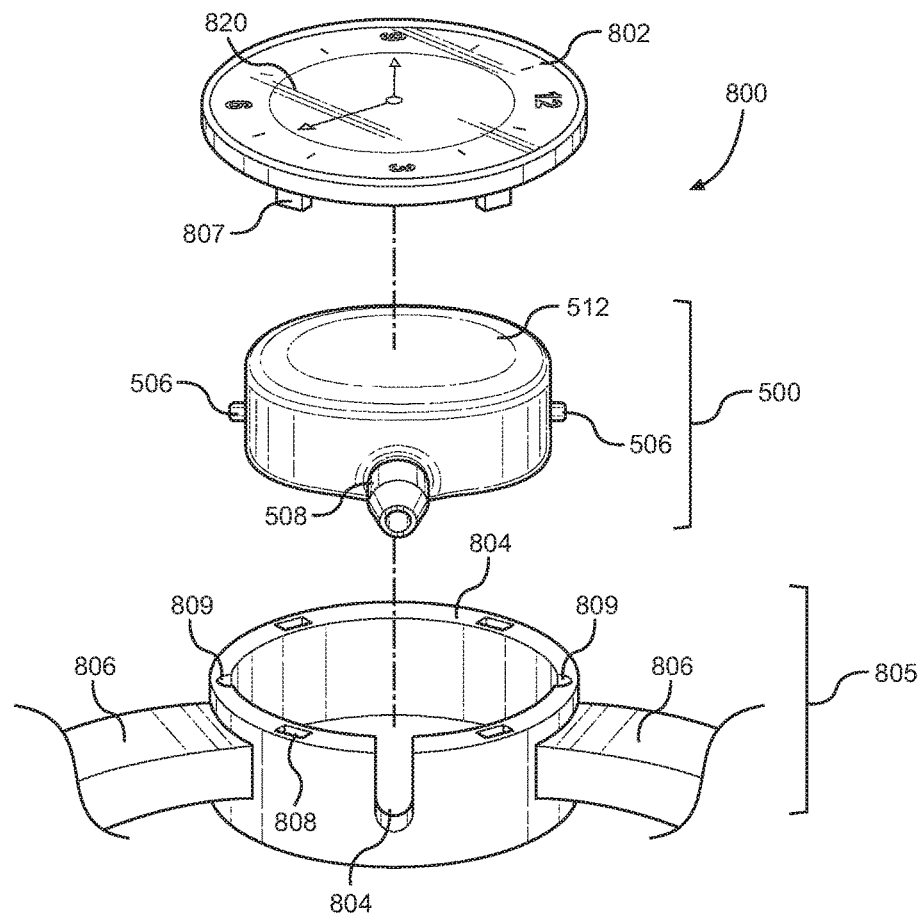
FIG. 31 is the exploded view of an alternative embodiment of liquid dispenser of the present invention, showing jewelry constructed in accordance with the invention and having a detachable face, jewelry base, and pump/valve device.

An alternative embodiment of the Liquid Dispenser That Can Be Worn As Jewelry of the present invention is shown in FIG. 31 and generally labeled 800. FIG. 31 is a perspective side exploded view of a watch, bracelet, or necklace. This embodiment consists of a detachable face 802 with an analogue watch 820, the pump/valve device 500, and a silicone jewelry assembly 805. The silicone jewelry assembly 805 consists of a silicone base 804 attached to a hollow silicone band 806 enclosing the liquid container (not shown). The valve/pump device 500 is located within the core of the silicone jewelry base 804. The valve/pump device 500 once positioned properly inside the silicone jewelry base 805 is covered by the detachable face 802.

The detachable face 802 is attached to the silicone jewelry assembly 805, by snapping into the silicone base 805 by sliding mounting tabs 807 into the mounting tab holes 808. The valve 508 seats in a valve channel 810 in the silicon base 805. The connectors 506 seat in connector holes 809 in the silicon base 805 where the connectors 506 can be connected to the hollow silicon band 806. However, the detachable face 802 can be attached to the silicone jewelry base 805 using any means known in the art including, but not limited to, a hinge, a threaded engagement, or friction fit.

Although depicted in FIG. 31 as watch, this alternative embodiment of the Liquid Dispenser that can be worn as Jewelry 800 can be configured into many jewelry pieces known in the art including, but not limited to, a necklace, bracelet or watch. The watch/bracelet bands will be hollow and the watch/bracelet face will be detachable. Similarly, when configured as a necklace, the necklace bands will be hollow and the necklace face will be detachable.

In operation, the necklace, watch, or bracelet of this alternative embodiment of the Liquid Dispenser That Can Be Worn As Jewelry 800 is worn on the patron. When the user is in need of the liquid (not shown), the user applies pressure to the detachable face 802, which, in turn, applies pressure on the flexible dome 512 (not shown) of the pump/valve device 500 (not shown). Pressure exerted on the flexible dome 512 causes liquid to be dispensed through the valve 508.

Figure 32:
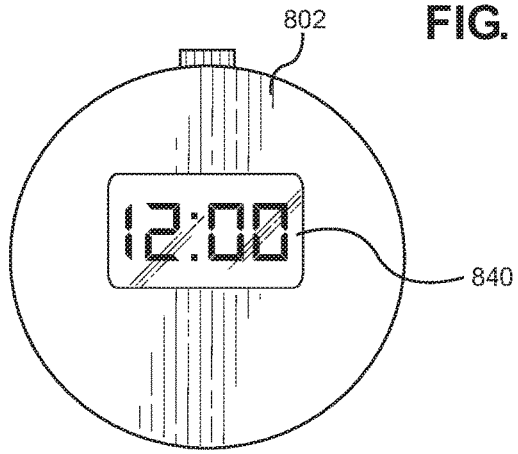
FIG. 32 is a front view of the detachable face of the alternative embodiment of liquid dispenser of the present invention shown in FIG. 31, and showing the detachable face with an alternative digital display and sized to enclose the pump/valve device within the jewelry base.
Figure 33:
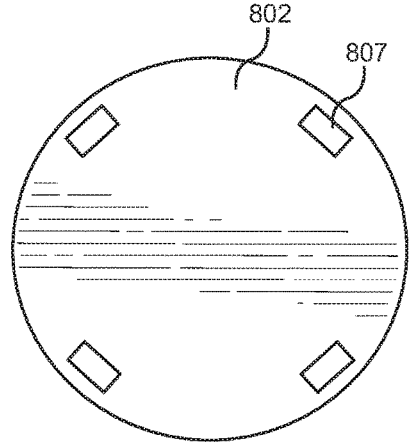
FIG. 33 is a perspective back view of the detachable face for a watch of the alternative embodiment of the present invention shown in FIG. 31, and showing the back of the pump/valve device which is covered by the detachable face.
Figure 34:
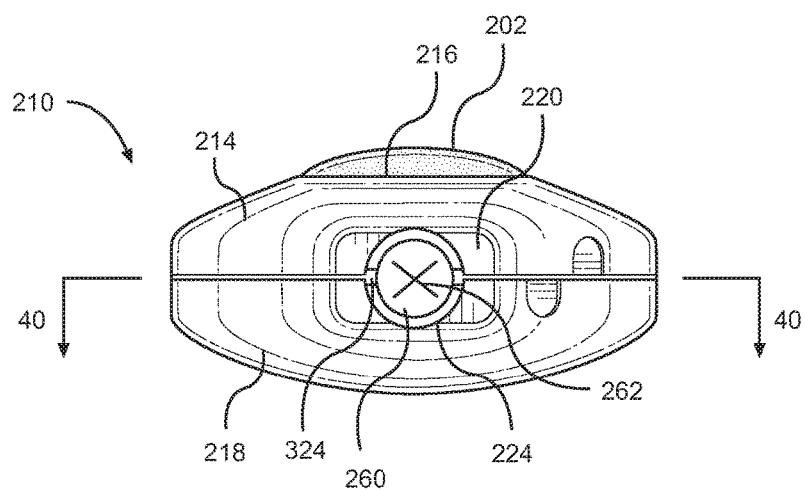
FIG. 34 is a front view of an alternative embodiment of a liquid dispenser having an outer shell enclosing a bladder assembly, the outer shell having an opening providing access to the flexible bladder of the bladder assembly, and a circular aperture in alignment with a cross-slit valve of the bladder assembly.
Figure 35:
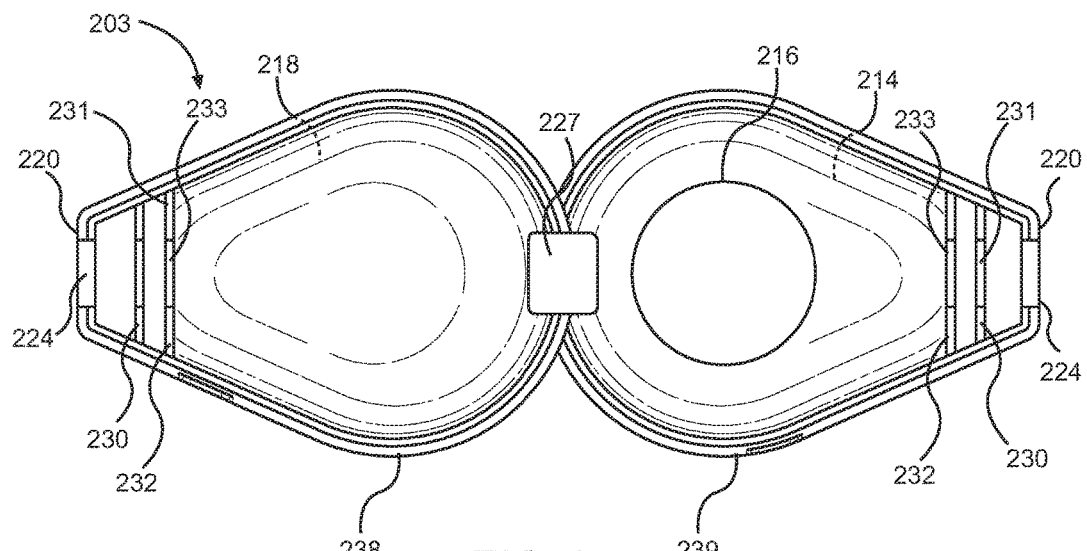
FIG. 35 is a top view of the liquid dispenser shown in FIG. 35 without the bladder assembly and showing the interior of both the anterior half and the posterior half of the outer shell, each half having a first support rib with a first semi-circular support surface and a second support rib with a second semi-circular support surface.
Figure 36:
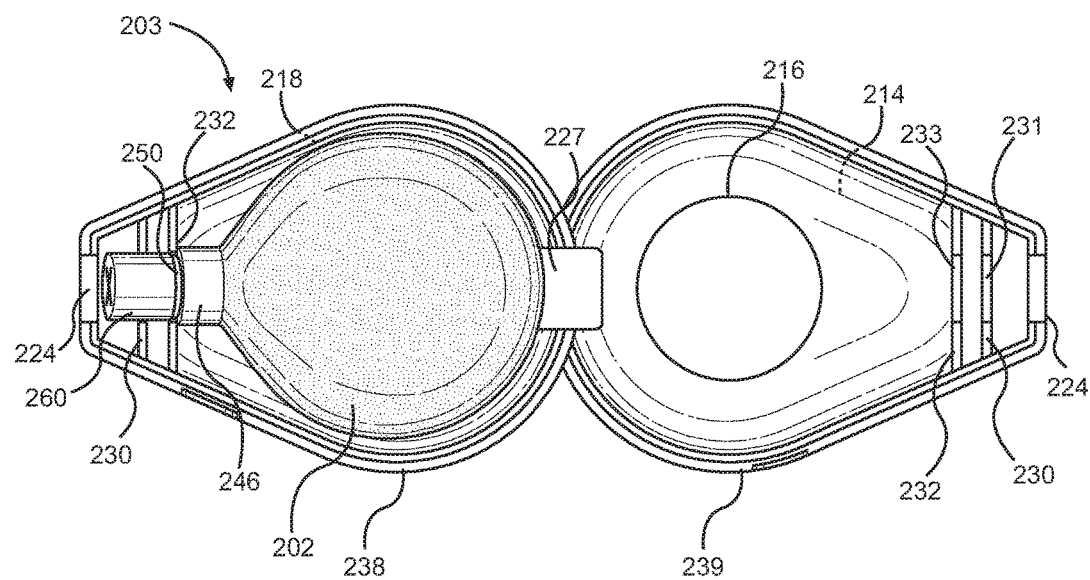
FIG. 36 is a top view of the liquid dispenser shown in FIG. 35 with the bladder assembly placed within the interior of the anterior half of the outer shell with the valve secured in the first semi-circular support surface and the second semi-circular support surface with the retention bulb of the flexible bladder secured against the second support rib.

FIG. 32 is a perspective front view of the detachable face 802. More specifically, FIGS. 32 and 33 are the top and bottom views of the detachable face 802 covering the pump/valve device 500. This detachable face 802 may be a digital clock, analog clock, or designed with many variations of colors and decorations. The detachable face 802 shown in FIG. 32 has a digital read out 840 and is flexible, and can compress when pressure is applied. FIG. 33 is a bottom view of the detachable face 802 showing mounting tabs 808. The bottom of the detachable face 802 may be a variation of different colors, designs, decorations, or will be the location for the battery for the watch. The pump/valve device 500 will be contained under the detachable face.

Referring to FIGS. 34 through 41, another alternative preferred embodiment of the Liquid Dispenser is shown and generally designated 210. As with previous embodiments, the Liquid Dispenser 210 has an outer shell 203 that encapsulates a bladder assembly 205 which is accessible through an opening 216 in the outer shell 203.

The bladder assembly 205 has a flexible bladder 202 having a retention bulb 246 on one end of the flexible bladder 202 with a neck 248 extending from the retention bulb 246. The neck 248 has a central passage 249 that runs along the length of neck 248 and is in fluid communication with the interior of the flexible bladder 202.

A sleeve 250, with a sleeve passage 259 extending throughout the sleeve 250, is slidably positioned on the neck 248 at the sleeve passage 259. Preferably, the sleeve passage 259 has a sleeve passage diameter that is slightly larger than the outer diameter of the neck 248 to facilitate the placement of the sleeve 250 on the neck 248. Once positioned on the neck 248, the sleeve 250 is permanently bonded to the neck 248 using sonic welding at bonding surface 252. The sleeve 250 is formed with a retention groove 254 sized to secure a valve 260. The sleeve 250 is positioned on the neck 248 such that the retention groove 254 of the sleeve is adjacent the retention bulb 246 of the flexible bladder 202.

Figure 37:
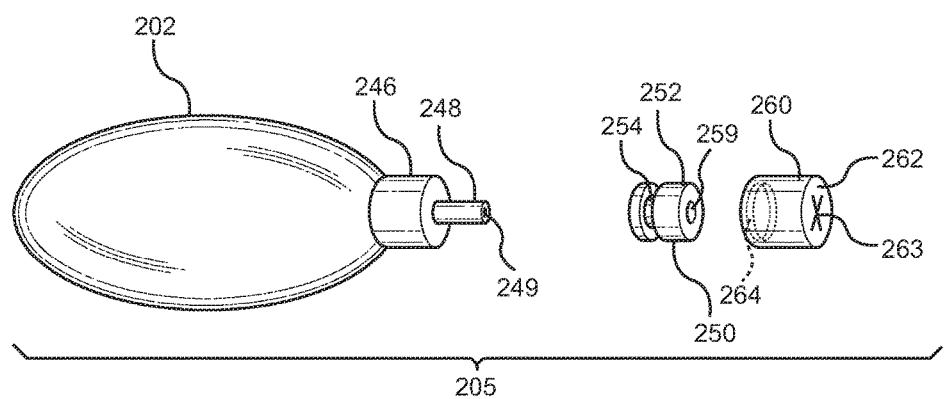
FIG. 37 is an assembly view of the bladder assembly shown in FIG. 36 and showing the flexible bladder with a retention bulb and a neck extending from the retention bulb, a sleeve sized to fit on the neck and equipped with a retention groove, and a valve having a retention ring opposite a cross slit opening with an opening tip.
Figure 38:
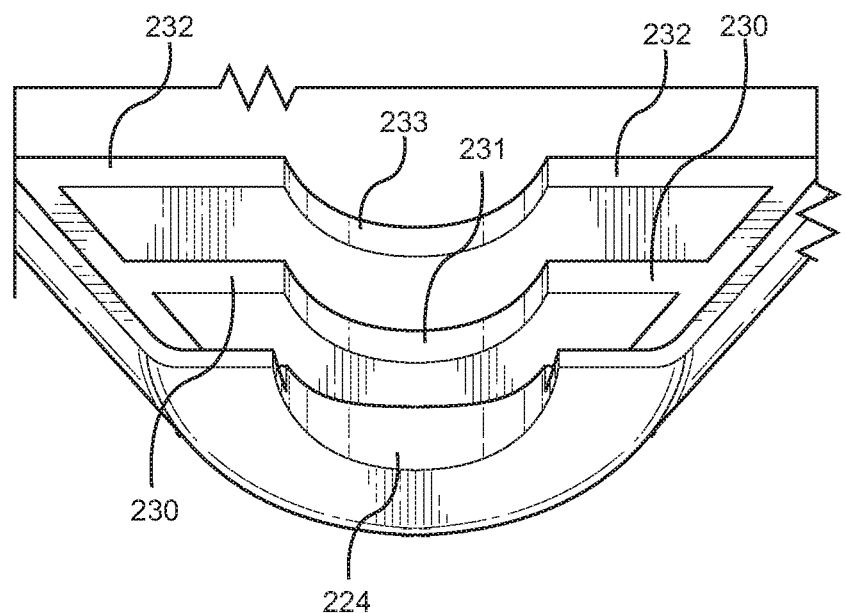
FIG. 38 is a close up front isometric view of the aperture, first support rib and second support rib of the anterior half of the outer shell show in FIG. 35.
Figure 39:
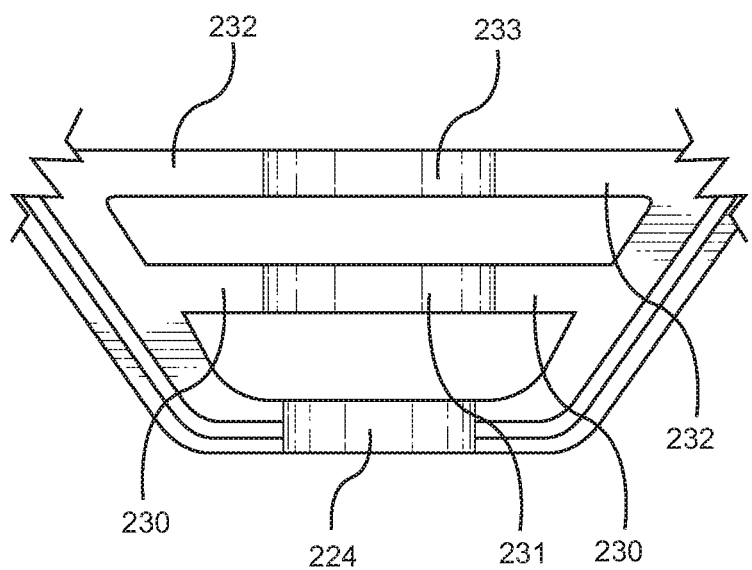
FIG. 39 is a top close up view of the aperture, first support rib and second support rib of the anterior half of the outer shell shown in FIG. 35.
Figure 40:
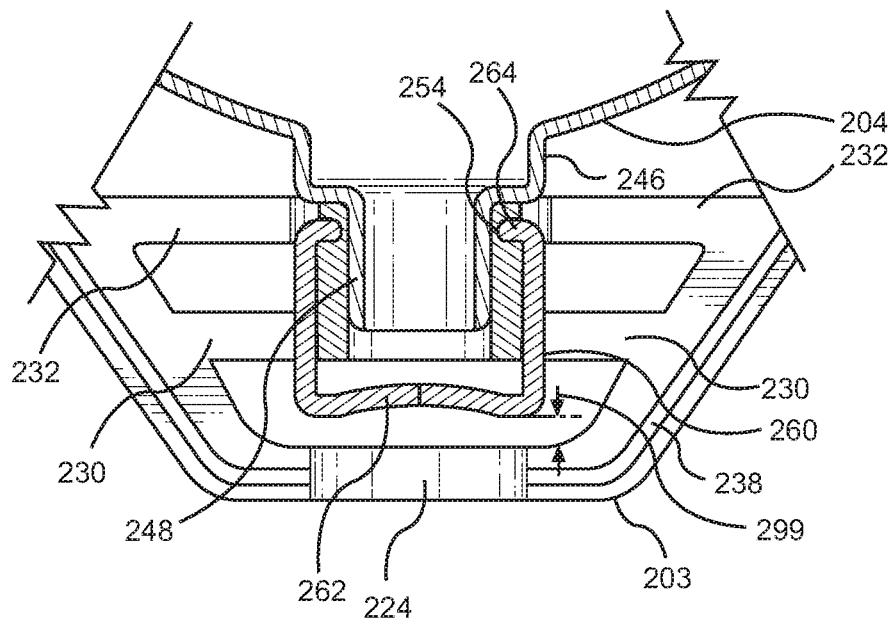
FIG. 40 is a top close up cross-sectional view of the valve end of the bladder assembly shown along the lines 40-40 in FIG. 34 positioned within the anterior half of the outer shell with the valve at a setback distance from the aperture of the outer shell and in the closed position.
Figure 41:
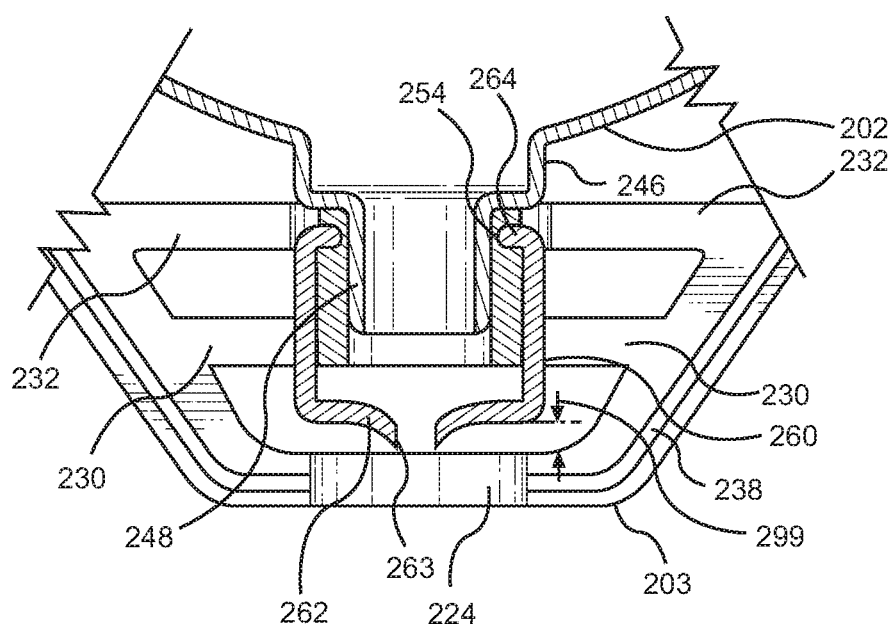
FIG. 41 is a top close up cross-sectional view of the valve end of the bladder assembly shown along the lines 40-40 in FIG. 34 positioned within the anterior half of the outer shell with the valve at a setback distance from the aperture of the outer shell and in the open position

The valve 260 depicted in FIG. 37 is a cross slit valve formed with a cross slit opening 262. The valve 260 is formed with a retention ring 264 formed within the inner diameter of the valve 260 and opposite the cross slit opening 262 with an opening tip 263. The retention ring 264 is sized to securely fit within the retention groove 254 of sleeve 250 thereby securing the valve 260 to the sleeve 250. The inner diameter of the valve 260 may be sized slightly smaller than the outer diameter of the bonding surface 252 of the sleeve 250 to facilitate an interference fit to further secure the valve to 260 to the sleeve 250. Once secured to the sleeve 250, the valve 260 is in fluid communication with the interior of the flexible bladder 202 through the central passage 249 of neck 248 allowing fluid stored in the flexible bladder 202 to be dispensed through the valve 260.

As with other embodiments shown herein, the outer shell has an anterior half 214 and a posterior half 218 that are connected together by a hinge 227. The anterior half 214 and posterior half 218 each has a flat surface 220 opposite the hinge 227 that each has an aperture 224 that forms an aperture 224 that is circular in shape when the outer shell 203 is closed. The interior surface of both the anterior half 214 and posterior half is formed with a first support rib 230 and a second support rib 232. The first support rib 230 has a first semi-circular support surface 231 that is aligned with and slightly larger than the aperture 224. The second support rib 232 has a second semi-circular support surface 233 that is aligned with the first semi-circular support surface 231. The first support rib 230 and the second support rib 232 are positioned in the anterior half 214 and the posterior half 218 such that when the outer shell 203 is closed the first support rib 230 in the anterior half 214 is aligned with and adjacent to the first support rib 230 in the posterior half 218 and the second support rib 232 in the anterior half 214 is aligned with and adjacent to the second support rib 232 in the posterior half 218. The first semi-circular support surface 231 and the second semi-circular support surface 233 constitute a valve receiver 234 sized to receive and secure a valve 260 within the outer shell 203.

In order for the outer shell 203 to remain securely closed during use, interior alignment ridge A 238 and alignment ridge B 239, fit together to keep the anterior and posterior halves 214 and 218 from shifting when closed.

When the outer shell 203 is closed, the valve 260 is secured within the outer shell 203 in the valve receiver 324 formed between the first semi-circular support surfaces 231 on the anterior half 214 and the posterior half 218. As the flexible bladder 202 is compressed by a user, the valve receiver 324 ensures that the opening tip 263 of the valve 260 remains centered with the aperture 224 of the outer shell 203.

The primary functions of the retention bulb 246 are to position the bladder assembly within the outer shell 203 and maintain a setback distance 299 between the opening tip 263 of the valve 260 and the aperture 224 of the outer shell 203. The maintenance of the setback distance 299 is crucial in order to ensure that the opening tip 263 of the valve 260 remains within the outer shell 203 so as to be protected from damage during use. This configuration allows for the continuous protection of the valve 260 without the need for a cap, which is easily lost. The setback distance 299 is maintained because the diameter of the retention bulb 246 is larger than the diameter of circle formed by the semi-circular support surfaces 233 and 231 in the anterior half 214 and posterior half 218 of the outer shell. As a result, the retention bulb 246 rests against the second support ribs 232 thereby preventing lateral movement of the valve 260 within the shell. The retention bulb 246 is sized to ensure that an adequate setback distance 299 is created when the bladder assembly 205 is placed within the outer shell 203.

To use the embodiments reflected in FIGS. 1 through 18 and 34 through 41, a user simply compresses the flexible bladder at the opening in the outer shell to dispense liquid from the valve and out the outer shell at the aperture without the burden of first needing to remove and store a cap or lid. It is to be appreciated that the novel features of the present invention enable a user to simply wear the liquid dispenser by connecting the same to a belt or necklace and quickly dispense liquid sanitizer without the burden of having to retrieve the liquid dispenser from a purse or pocket. When a bladder assembly is depleted of hand sanitizing liquid, the shell is simply opened and the bladder assembly is quickly removed and discarded.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

While there have been shown what are presently considered to be preferred embodiments of the present invention, it will be apparent to those skilled in the art that various combinations of preferred embodiments, changes and modifications can be made herein without departing from the scope and spirit of the invention.

The invention claimed is:

1. A liquid dispenser comprising:
   a bladder assembly having a flexible bladder with a retention bulb and a neck extending from said retention bulb wherein said flexible bladder is capable of storing a fluid and is in fluid communication with a valve secured to said neck wherein said valve has an opening tip;
   an outer shell with an anterior half and a posterior half connected together by a hinge system enclosing said bladder assembly and having an aperture sized to receive said opening tip of said valve;
   one or more attachment brackets connected to said outer shell;
   an access through said outer shell to enable a user to apply a force to said flexible bladder sufficient to open said opening tip of said valve;
   wherein said posterior half of said outer shell and said anterior half of said outer shell each has a valve receiver made up of one or more support ribs having a semi-circular opening sized to receive and secure said valve within said outer shell such that said opening tip of said valve is centered with said aperture and housed within said outer shell at a setback distance from said aperture of said outer shell regardless of whether said valve is open or closed and wherein said setback distance is maintained by said retention bulb positioned adjacent to at least one of said at least one or more support ribs; and;

wherein said valve is secured to said neck by a sleeve bonded to said neck wherein said sleeve has a retention groove and said valve is formed with a retention ring opposite said opening tip of said valve and wherein retention ring is secured within said retention groove.

2. The liquid dispenser of claim 1 wherein said access is an opening through said anterior half of said outer shell and wherein said one or more attachment brackets is at least one bail.

3. The liquid dispenser of claim 2 wherein said posterior half of said outer shell and said anterior half of said outer shell each has an alignment ridge.

4. The liquid dispenser of claim 3 wherein said sleeve is secured to said neck of said flexible bladder by way of sonic welding.

5. The liquid dispenser of claim 4 further comprising a first opening indentation on said posterior half of said outer shell and a second opening indentation on said anterior half of said outer shell.

6. The liquid dispenser of claim 5 wherein said opening tip of said valve is a cross-slit.

\* \* \* \* \*